(12) United States Patent
Kechagia et al.

(10) Patent No.: US 7,514,046 B2
(45) Date of Patent: Apr. 7, 2009

(54) METHODS AND SYSTEMS FOR PROCESSING MICROSCALE DEVICES FOR REUSE

(75) Inventors: Persefoni Kechagia, San Carlos, CA (US); Michael Greenstein, Los Altos, CA (US); Bruce Brogden, Pleasanton, CA (US); Ed Donlon, San Jose, CA (US); Masayoshi Hayashi, Hyogo (JP); Aaron J. Rulison, Mountain View, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 695 days.

(21) Appl. No.: 10/861,784

(22) Filed: Jun. 4, 2004

(65) Prior Publication Data

US 2005/0019213 A1 Jan. 27, 2005

Related U.S. Application Data

(60) Provisional application No. 60/546,593, filed on Feb. 20, 2004, provisional application No. 60/492,496, filed on Aug. 4, 2003.

(51) Int. Cl.
*B01L 1/00* (2006.01)
(52) U.S. Cl. .................. 422/102; 134/26; 134/22.1
(58) Field of Classification Search ............... 134/22.1, 134/26; 422/102
See application file for complete search history.

(56) References Cited

U.S. PATENT DOCUMENTS

| | | | |
|---|---|---|---|
| 4,493,896 A * | 1/1985 | La Motte et al. ......... 435/283.1 |
| 4,649,946 A | 3/1987 | Yano | |
| 5,681,484 A | 10/1997 | Zanzucchi et al. | |
| 5,851,370 A | 12/1998 | Maracas et al. | |
| 5,872,010 A * | 2/1999 | Karger et al. ............. 436/173 |
| 6,400,272 B1 | 6/2002 | Holtzman et al. | |
| 7,252,928 B1 * | 8/2007 | Hafeman et al. ............ 435/4 |
| 2001/0005489 A1 | 6/2001 | Roach et al. | |
| 2003/0116024 A1 * | 6/2003 | Francia .................... 99/275 |
| 2003/0211012 A1 | 11/2003 | Bergstrom et al. | |

FOREIGN PATENT DOCUMENTS

| | | |
|---|---|---|
| EP | 1360992 A2 | 11/2003 |
| WO | WO 94/26432 A1 | 11/1994 |
| WO | WO-02/089981 A2 | 11/2002 |
| WO | WO 02/089981 A2 * | 11/2002 |
| WO | WO-03/021230 A2 | 3/2003 |

OTHER PUBLICATIONS

Christie J. Geankoplis, "Transport Processes and Unit Operations", Prentice Hall P T R, Third Edition, p. 31.*

* cited by examiner

*Primary Examiner*—Frankie L Stinson
*Assistant Examiner*—Samuel A Waldbaum
(74) *Attorney, Agent, or Firm*—Cardinal Law Group

(57) ABSTRACT

This invention provides methods and systems for flushing, washing, and priming microscale devices for reuse. Washing and priming methods include flowing solutions from a manifold to flush wells and microchannels of a microfluidic chip. Systems include manifolds adapted to seal and flow solutions or gasses into chip wells. Devices include microfluidic devices with data storage modules to track the reprocessing status of the microscale devices.

28 Claims, 11 Drawing Sheets

METHODS AND SYSTEMS FOR PROCESSING MICROSCALE DEVICES FOR REUSE

CROSS REFERENCE TO RELATED APPLICATIONS

This application claims priority to and benefit of a prior U.S. Provisional Application No. 60/546,593, "Methods and Systems for Processing Microscale Devices for Reuse", by Kechagia et al., filed Feb. 20, 2004, and to prior Provisional Application No. 60/492,496, "Use of Cleansers to Recondition Microfluidic Chips," by Rulison, filed Aug. 4, 2003. The full disclosure of the prior applications are hereby incorporated by reference in their entirety.

FIELD OF THE INVENTION

The present invention is in the field of systems and methods for reprocessing analytical system components for reuse. In particular, the invention provides systems and methods for flushing, washing, and reusing microfluidic chips.

BACKGROUND OF THE INVENTION

Microfluidic chips are generally disposable devices due to the problems presented in reprocessing them for repeated use. Reuse of microchips can be impractical because of handling problems, buildup of reagent constituents in the chips, and the introduction of other variables with repeated use that can cause inconsistent results.

Microfluidic chips used in many microfluidic instruments are a small part of the overall instrument and can be relatively inexpensive. The automated manufacturing processes for microfluidic chips can reduce their cost and can provide consistent analytical results between runs on different chips. In many cases, microfluidic chips are considered "disposables" associated with microfluidic analyses. However, the cost of chips and the generation of waste in large microfluidic assay projects can add up to a significant expense. Moreover, there is much to be said for running comparative experiments on the same hardware.

Attempts have been made to wash and reuse microfluidic chips. Labs with small budgets and low labor costs have been known to manually wash chips. Chip makers have been known to manually wash microfluidic chip prototypes. Nevertheless, manual washing can be highly problematic. Manual microfluidic chip washing can proceed on a lab bench with a technician manually pipetting microliter wash solution volumes in and out of individual millimeter scale reagent wells, and flushing microchannels with syringes inserted through portals. However, problems often arise due to the uncontrolled environment and inconsistency of manual procedures. For example, particles in the environment can enter the chip and clog microchannels, bubbles can be unintentionally introduced into the chip, and use of reagents and accumulation of hazardous wastes can be excessive. Inconsistent manual processing can result in difficulty validating procedures and low confidence in results. The time, effort and expense of manual microfluidic chip reprocessing can be prohibitive.

Careful records should be maintained regarding the identification and use of reprocessed microfluidic chips so that the usable life of the chips is not unintentionally exceeded, possibly resulting in corruption of analytical results. Currently, the method typically employed for such record-keeping requires each individual user of the microfluidic device to maintain a detailed log listing which microfluidic chip is used, the purpose for which the device has been used, and the number of samples handled during use. This record-keeping method has several limitations. For example, a user may simply fail to record a use. Also, an identification label affixed to the surface of the microfluidic chip may become lost or illegible due to wet storage of the microfluidic chip, resulting in an inability to identify the microfluidic chip. If an identification label is affixed to the package for storing the microfluidic chip, the wrong device may be placed into the package.

In view of the above, a need exists for consistent, reliable and controlled methods to process microfluidic chips for reuse. It would be desirable to have systems that reduce the expense and waste involved in cleaning microfluidic chips for reuse. Benefits can be provided by systems and methods that efficiently and reliably track the use history of microfluidic chips. The present invention provides these and other features that will be apparent upon review of the following.

SUMMARY OF THE INVENTION

The present invention provides systems and methods useful in processing microscale devices for use or reuse. Systems can include, e.g., manifolds with mesoscale flow paths for solutions to flow through orifices to wells and/or channels of microscale devices. Methods of the invention can include, e.g., providing a manifold with mesoscale flush channels and/or waste channels in fluid contact with one or more orifices, contacting wells of a microscale device with the orifices, and flowing process solutions from the flush channels through the orifices to the wells to prepare the microscale device for use or reuse. The systems and methods of the invention can, e.g., flush storage solutions from a microscale device, prime the device with working solutions, flush end process solutions from the device, wash channels and surfaces of the device, and/or fill the device with storage solutions.

A system of the invention for processing a microscale device can include, e.g., a manifold with one or more mesoscale flush channels or one or more mesoscale waste channels, one or more orifices in fluid contact with the flush channels or waste channels and adapted to functionally contact one or more wells of the microscale device, and one or more process solutions in a flowpath that includes: the mesoscale channels, the orifices, and the wells of the microscale device. The Flowpath of the system can optionally include, e.g., the microscale channels of the device and/or the mesoscale waste channels of the manifold.

The system can have an automated flow controller, e.g., to select process solutions, configure flow paths, control flow rates, and control flow times in a predetermined logical fashion. The automated flow controller can include, e.g., a computer in functional communication through an interface to actuators such as solenoid valves, pneumatic valves, pressure regulators, device handlers, and/or the like. The actuators can be functionally associated with manifolds of the system to control process solution flows into and/or out from microscale devices. The systems of the invention can be, e.g., free standing independent instruments or can be integrated into an analytical instrument as a component (e.g., a subsystem).

The manifolds of the systems can provide, e.g., flow path segments between process solution reservoirs and wells of microscale devices. The manifolds can be multilayer structures with channels running in three dimensions, connections to solution supply containers, and/or mounting positions for control actuators. Manifolds can receive pressurized solutions from reagent containers, and provide an appropriate flow path through mesoscale channels and orifices to wells of a microscale device. The flow paths in the manifolds can include mesoscale channel segments having one or more dimension (e.g., width and/or depth) ranging from about 5 mm to about 0.1 mm. Such mesoscale channels can be, e.g., small enough to minimize solution dead volumes and to allow complex three dimensional networks in a small manifold, but large enough minimize clogging problems while providing flows adequate to quickly flush process solutions through one or more wells or microscale channels of a microscale device. Solution or gas flows in the mesoscale flush channels or waste channels can be driven, e.g., by a pressure differential between solution reservoirs and orifices. In one aspect of the invention, a flush channel can be axially concentric with a waste channel, e.g., to share access to a well at a common orifice.

Mesoscale channels of a system manifold can terminate at one or more orifice. The orifices can supply and/or remove solutions at microscale device wells, such as, e.g., sample wells, reagent wells, waste wells, and/or the like. An orifice can be, e.g., a nozzle that seals to a microscale device well to inject and/or remove process solutions. The process solutions can be, e.g., wash solutions, storage solutions, or reagents to condition or prime the wells or microchannels. The process solutions can include, e.g., NaOH, water, reagents, surfactants, solvents, heated solutions, and/or the like. The orifices can be adapted to functionally contact (e.g., seal with or position in close proximity to) the wells by providing, e.g., o-rings and/or tapered surfaces complimentary to well surfaces. The orifices can have, e.g., one or more radial jets, e.g., uniformly directing process solutions or flushing gasses onto well walls for efficient flushing of the wells.

In a preferred embodiment, the system manifolds can be configured with concentric ring reservoirs receiving solutions from reagent containers through solution supply ports and feeding the solutions to orifices through radially oriented mesoscale channels. For example, two or more concentric ring reservoirs can be in fluid contact with the flush channels or waste channels with their solutions sharing a flowpath in one or more channel segments. Sharing of flow paths typically consists of a logical sequential time sharing of mesoscale channel segments controlled by control valves during the progression of processing steps.

Manifolds of the systems can have, e.g., one or more control valves in communication with the automated flow controller and functionally associated with the flush channels or waste channels. Control valves are often three-way valves, located at an intersection between channels flowing from two or more ring reservoirs, normally open to a channel from one ring reservoir and normally closed to a channel from another ring reservoir. The control valves can control flows of the process solutions (or flushing gasses) to or from, e.g., individual wells, two or more wells, or groups wells with common process solution handling requirements. For example, a single control valve can control a channel intersection to or from groups of sample wells, reagent wells, wash wells, waste wells, and/or the like. The control valves can be any suitable valves, such as, e.g., pneumatic valves, solenoid valves, needle valves, sandwich valves, diaphragm valves, slider valves, ball and seat valves, etc.

Process solutions can be flushed from channels and wells of the systems using gasses flowing along pressure differentials in a flow path. One such system can include, e.g., a manifold with one or more mesoscale flush channels or one or more mesoscale waste channels, one or more orifices in fluid contact with the flush channels or waste channels and adapted to functionally contact one or more wells of the microscale device, and a gas in a flowpath with a pressure differential and comprising: the one or more mesoscale channels, the one or more orifices, and the one or more wells of the microscale device so that process solutions or waste solutions are flushed from the manifold, wells, or microfluidic device. The contact between the orifices and the wells can be a sealed contact so that, e.g., the pressure differential can continue between a flush channel and waste channel through a well. Part or all of the pressure differential can be provided by a vacuum source, for example, by a vacuum (pressure less than atmospheric pressure) source in fluid contact with a waste channel. Pressure differentials across gas flushing flow paths can range, e.g., from about 1 psi to about 500 psi. The flowpaths can include one or more microchannels.

The present invention includes data storage modules mounted to the microscale devices. Systems of the invention can include a microscale device with a data storage module, e.g., to receive, store, and/or supply information relevant to the use of microscale devices. For example, a microscale device with microscale channels can have a data storage module including a counter for counting a number of uses or washes of the microscale device. The microscale device can be capable of functional contact with processing manifold orifices. The data storage module can be mounted in an orientation adapted to facilitate communication with a data reader. For example, the data storage module can be mounted to the microscale device (e.g., a microfluidic cartridge) by mounting it to a mounting plate which holds a microfluidic chip, or the data storage module can be mounted to the microscale device by mounting it directly to the microscale device. In a preferred embodiment, the data storage module is a radio frequency identification (RFID) tag.

The data storage module can hold any data useful in the operation of a microscale device or associated systems. The data storage module can include a programmable memory, e.g., programmable by a reader or other device in communication with the module. Data stored by the module can include, e.g.: device identification data, device usage data, sample analysis data, process cycle data, part numbers, serial numbers, work order numbers, device design numbers, calibration data, manufacture dates, expiration dates, usage limit numbers, error codes, and/or the like. For example, the data storage module can be configured to count and store a number of wash cycles of the microscale device. In a preferred embodiment, the microscale device can be used two or more times and the data storage module can provide a usage count incremented with each use. In another preferred embodiment, the use of the microscale device is discontinued when the number of wash cycles reaches a predetermined number stored in the programmable memory.

A reader can be provided to communicate with data storage modules in microscale devices. The reader can include components, such as, e.g., a radio frequency transmitter, a radio frequency receiver, an antenna, a data processor, a user interface, an optic fiber, a light transducer, and/or electrical connections to the data storage module. The reader can, e.g., energize the module and/or send data to the data storage module using the transmitter. The reader can be integrated into the microscale device, can be hand held, or can be integrated into a separate instrument for communication with the data storage module.

The present invention includes methods for processing microscale devices for use or reuse. For example, the invention includes methods of processing a microscale device by providing a manifold with one or more mesoscale flush channels or mesoscale waste channels, providing orifices in fluid contact with the flush channels or waste channels and adapted to functionally contact wells of the microscale device, contacting the wells with the orifices, and flowing one or more process solutions through the flush channels into the wells to process the wells and/or one or more microchannels of the microscale device. In preferred embodiments, wells and microchannels of a microscale device are washed with wash solutions and primed with analytical reagents from flush channels of a manifold before reuse of the device. Microscale devices can be effectively processed for use 5 times, 10 times, 20 times, 30 times, or more using methods of the invention.

In a typical embodiment of processing a microscale device for reuse, a manifold is provided that has two or more orifices arranged on the manifold in a configuration adapted to functionally contact two or more wells of the microscale device at once, the orifices are positioned to functionally contact the wells, a process solution is flowed from the manifold flush channels through the orifices into the wells and out through manifold waste channels and/or through one or more microchannels of the microscale device. In methods for processing two or more wells at a time, the manifold orifice arrangement can be fixed to conform with the orientation of a predetermined set of wells, or can be adjustable to comply with different well orientations on different microscale devices. In typical embodiments, the orifices on the manifold and/or wells on the microscale device range in number from about 2 to about 32, 34, or more.

In another embodiment, methods of the invention for reprocessing a used microscale device can include: positioning the microscale device in functional contact with a manifold, flowing one or more process solutions from the manifold to the microscale device to wash one or more wells or microscale channels in the microscale device, priming the microscale device with priming solutions, and reusing the microscale device.

Manifolds can be fabricated in the methods of the invention, e.g., by techniques, such as machining, mold injection, lithography, layered construction, etching, and/or the like. The manifolds can be fabricated to include mesoscale flush and/or mesoscale waste channels having a dimension ranging from about 5 mm to about 0.1 mm.

Process solutions can flow in the manifold channels, e.g., under the force of a pressure differential across the mesoscale channels and/or through flow paths established by control valves in the channels. The process solutions used in the methods can include, e.g., NaOH, water, surfactants, reagents, solvents, high temperature solutions, and/or the like. In a preferred embodiment, microscale devices that have suffered certain failure modes or the presence of debris in channels can be reconditioned by flushing the device with an alkaline wash solution containing a combination of an ampholytic surfactant and a chelator. One such alkaline wash solution can be, e.g., Hellmanex II, (Hellma GmbH & Co KG; Müllheim, Germany) a composition of wetting agents, emulsifiers, ampholytic surface-active agents, complexing agents, and potassium phosphate. The process solutions can be forced into wells, such as, e.g., sample wells, reagent wells, or waste wells, to flush, wash, prime, or prepare them for storage.

Providing orifices adapted to functionally contact the wells in the methods of the invention can include, e.g.: providing O-rings between the orifices and wells, providing tapered well walls, providing tapered orifices fitted to well walls, or providing a waste channel flow adequate to prevent overflow of process solutions from the wells. In a preferred embodiment, O-rings fitting between the orifices and well walls form a seal capable of transmitting pressure differentials between the manifold and a microscale device. In one embodiment, an orifice is sealed to a well and solutions or gasses under pressure can be directed to flow from the orifice and out of the well alternately through a waste channel of the manifold or through a microchannel of the microscale device. In such a case, the flow of the pressurized solution or gas can be optionally be directed to the microscale channels by closing a control valve in an alternate outlet mesoscale waste channel. In another aspect, gasses or process solutions can flow through one or more radial jets in the orifices to increase the efficiency of well wall flushing.

Methods of the invention can include provision of ring reservoirs and control valves to provide desired flows of process solutions. Ring reservoirs can be in fluid contact with orifices through control valves and flush channels or waste channels. Flow rates and flow paths of process solutions or gases through the channels can be controlled, e.g., by regulating pressure differentials across channel segments and/or by adjusting control valves in the channels. Control valves can each control flows of solutions or flush gasses to individual wells or control more than one channel branches that terminate at particular groups of wells. A control valve located in a waste mesoscale channel can be used to alternately direct process solutions to flow into a waste ring reservoir when open or to flow into microchannels of a well when closed. In many instances, it is preferred to process the wells before processing the microchannels.

Control systems can flexibly control flows of multiple solutions to multiple wells with precise timing. In an aspect of the invention, the flow in the flush channels or the waste channels can be controlled so that two or more wells receive: a different amount of process solution, a different type of process solution, different flushing gas flows, and/or a process solution at a different time.

Methods of the invention can include flushing flowpaths with flushing gasses. Pressure differentials can be established along flowpaths to flush process solutions from, e.g., supply lines and ports, ring reservoirs, mesoscale flush channels, wells, mesoscale waste channels, and/or microchannels. Methods of flushing process solutions from manifolds and/or microscale devices can include providing a manifold with one or more mesoscale flush channels or mesoscale waste channels, providing one or more orifices in fluid contact with the flush channels or waste channels and adapted to functionally contact one or more wells of the microscale device, contacting the one or more of the wells with the one or more orifices, and flowing a gas through a flowpath comprising the one or more wells and the flush channels or waste channels to flush process solutions from: one or more mesoscale channels of the manifold, the one or more wells, and/or one or more microchannels of the microscale device. Microchannels are typically flushed with gasses by sealing a manifold orifice to a well in fluid contact with the microchannel and providing a pressure to force solutions to waste.

Methods of the invention can effectively flush and wash wells and microchannels of a microscale device. Assay solutions, such as test samples or analytical reagents, can be cleared from well and channel volumes and surfaces to a high degree of efficiency. For example, processing a microscale device using methods of the invention can reduce an analyte in wells, and/or in microscale channels, by a million-fold or to less than 1 part per million (ppm).

DEFINITIONS

Before describing the present invention in detail, it is to be understood that this invention is not limited to particular devices or methods, which can, of course, vary. It is also to be understood that the terminology used herein is for the purpose of describing particular embodiments only, and is not intended to be limiting. As used in this specification and the appended claims, the singular forms "a", "an" and "the" can include plural referents unless the content clearly dictates otherwise. Thus, for example, reference to "a component" can include a combination of two or more components; reference to "a reagent" can include mixtures of reagents, and the like.

Unless defined otherwise, all technical and scientific terms used herein have the same meaning as commonly understood by one of ordinary skill in the art to which the invention pertains. Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

The term "mesoscale", as used herein, refers to dimensions ranging from about 5 mm to about 0.1 mm. Mesoscale channels can have, e.g., a diameter, width, and/or thickness in the mesoscale range.

The term "microchannels", as used herein, refers to channels having a dimension in the microscale range, e.g., from about 500 µm to about 0.1 µm.

The term "microscale device", as used herein, refers to a device comprising one or more microchannels. Typical microscale devices are, e.g., a microfluidic chip, or a microfluidic cartridge.

The term "microfluidic cartridge", as used herein, refers to a microscale device comprising a microfluidic chip mounted to a mounting plate (e.g., a caddy).

The term "data storage module", as used herein, refers to a device that can retain information. Typically, data storage modules of the invention are electrical or mechanical devices that can retain and indicate an identifier, current status, or event count. Many embodiments of data storage modules of this invention include components with electronic memories, such as integrated circuits. In a preferred embodiment, the data storage module is a radio frequency identification (RFID) tag that can receive instructions or transmit information to a reader.

The term "orifice", as used herein, refers to the region of a mesoscale flush channel or mesoscale waste channel where it terminates on or near the external surface of a manifold of the invention. An orifice is typically arranged on the manifold surface in a suitable orientation to functionally contact wells of microscale devices to provide and/or remove solutions and/or gasses. In some embodiments, an orifice can be a protruding element, such as a pipette tip or nozzle, for dispensing solutions to, or removing solutions from, one or more wells of a microscale device.

The term "radial jets", as used herein, refers to outlets from a flush channel radially arrayed on an outer surface of an orifice. Radial jets can be arrayed, e.g., to direct flows onto well walls for uniform flushing of well walls and spaces between an orifice and a well. Optionally, radial jets can be in fluid contact with waste channels to uniformly remove solutions or gasses from wells.

The term "well", as used herein, refers to a port of fluid access into a microscale device. Wells are typically holding chambers on the top of a microscale device that receive and hold solutions, such as, e.g., reagents, buffers, samples, controls, references, wash solutions, waste solutions, and/or the like, used in the operation of the device. Those skilled in the art can appreciate that some microscale devices may not have typical microfluidic cartridge wells at ports of fluid access; therefore, any sealable port of fluid access to a microscale device can be considered a "well" of the invention.

DETAILED DESCRIPTION

Figure 1:
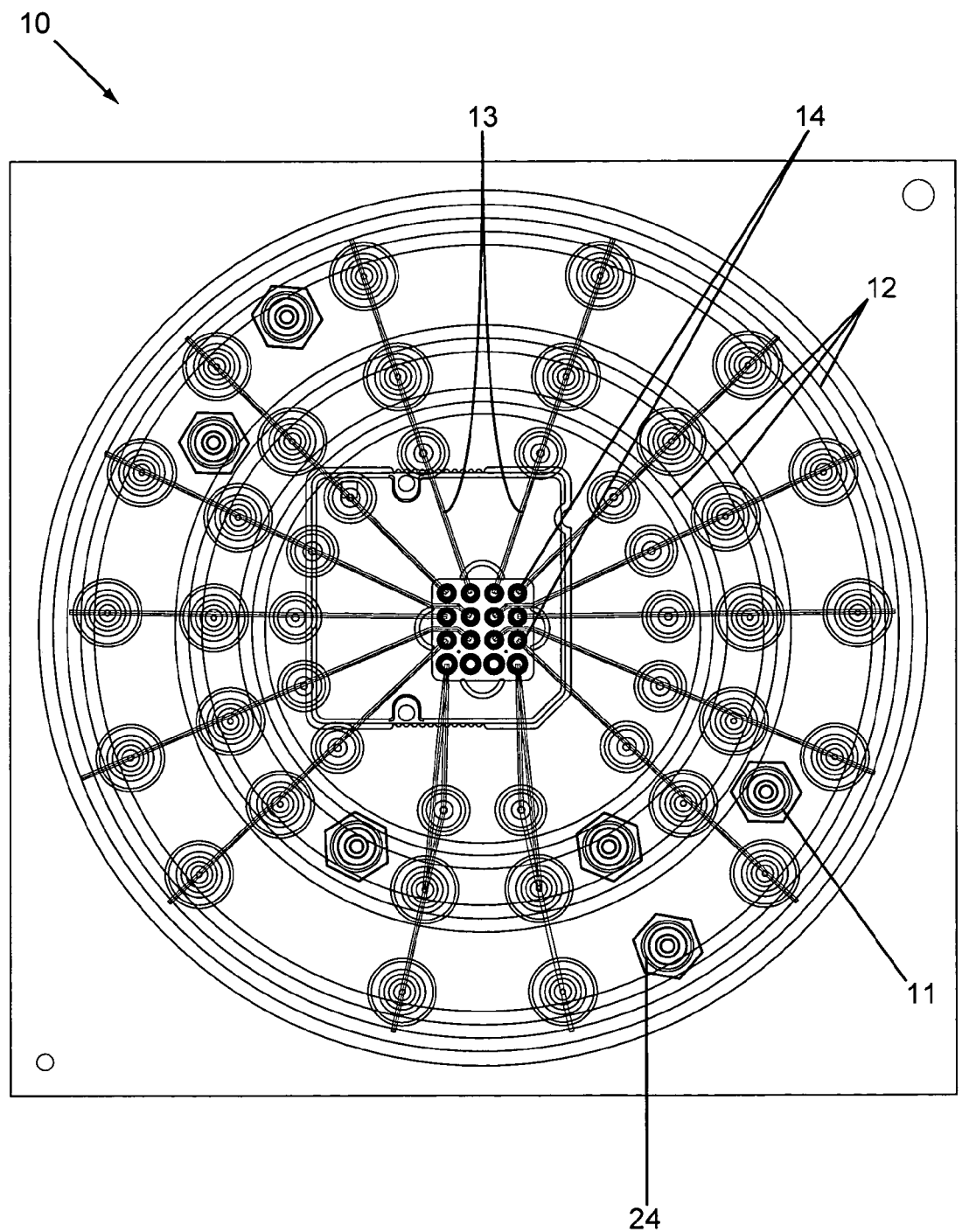
FIG. 1 is a schematic diagram of an exemplary manifold design.

During normal use of microscale devices, exposure of the wells and microchannels to assay solutions can result in chemical reactions and build up of solution constituents on surfaces. For example, proteins, hydrophobic constituents, polymers, and/or ionic groups can be adsorbed onto well and channel walls. Particles can enter the device to restrict flows. Particularly with reuse, build up of solution constituents can begin to affect flows and/or detector sensitivity resulting in a loss of sensitivity, precision, and reproducibility.

The present invention provides methods and systems for washing and/or priming microscale devices for reuse. Methods of the invention can include, e.g., provision of a manifold with mesoscale channels in fluid contact with orifices adapted to seal with wells of a microscale device, positioning the orifices to seal with the wells, and flowing one or more solutions into the wells to wash or prime the microscale device. Systems of the invention generally include, e.g., manifolds with mesoscale channels leading to one or more orifice to deliver solutions and/or flushing gasses through a controlled flowpath to wells of a microscale device. Systems and methods can employ data storage modules to track wash or use cycles for quality control purposes.

System for Reprocessing Microscale Devices

Systems for reprocessing microscale devices in the invention generally include computer directed flows of solutions through reservoirs and valves, to mesoscale channels in manifolds, and out from orifices adapted to seal with wells of the microscale device. The systems can have an efficient layout of reservoirs and channels to reduce consumption of solutions and shorten processing times. The systems can have control components that process information and logically direct flows for efficient and consistent reprocessing of microscale devices.

The systems can process microscale devices for reuse by directing flushing gasses, wash solutions, and/or priming reagents to wells and/or microchannels of the devices. Microscale devices of the invention include, e.g., microfluidic chips having channels with a dimension in a microscale range from about 0.5 µm to about 500 µm, from about 1 µm to about 500 µm, or from about 10 µm to about 100 µm. The microscale devices can include, e.g., microchannels leading from wells or ports at the exterior of the device to functional channel regions, such as incubation channels, separation channels and detection channels, and out to a waste well. Microscale devices can include, e.g., wells that hold solutions, such as wash solutions, analytical reagents, samples, waste, controls, and the like. Systems of the invention can have manifolds adapted to seal to wells, or other ports in fluid contact with channels of a microscale device, for sequential application of gasses or solutions to process (flush, wash, and/or prime) the device for reuse.

In a typical system, for example, process solutions are held in macro-scale reagent bottles and directed under automated control to ring reservoirs in manifolds of the invention. The solutions sequentially flow from the ring reservoirs through mesoscale channels controlled by automated valves to orifices sealed to wells of a microscale device. Pressure differentials can be directed across mesoscale channels of the manifold and/or microscale channels of the microscale device, to induce flows as desired. For example, a process solution can flow from a pressurized reagent bottle, through a ring reservoir, past an open control valve, out a manifold orifice, and into a well of a microscale device. The process solution can flush and wash the well before being removed from the well through a mesoscale waste channel into a waste reservoir under vacuum (relative low pressure). Optionally, the process solution can flow from the orifice sealed to the well to continue flowing under pressure through microchannels of the microscale device.

Systems of the invention can be stand alone appliances or can be, e.g., integrated into microfluidic analytical instruments that employ microscale devices. A stand alone system for reprocessing microscale devices can receive, e.g., stacks of used microscale devices from several analytical instruments for reprocessing of each device in turn. The microscale devices can be transported to and from the instruments by technicians, robotic devices, or by conveyor systems. The system can communicate with data storage modules coupled to the microscale devices to, e.g., track use cycles and/or to designate washing and priming parameters appropriate to each particular microscale device. Optionally, systems of the invention can be dedicated components incorporated into an apparatus employing a microscale device.

Manifolds

Manifolds of the invention provide efficient flow control of solutions, e.g., from reagent bottles, to ring reservoirs, through mesoscale channels, past control valves, and out from orifices to wells of microscale devices. In some embodiments of the invention, the manifolds can provide flow control of flushing gasses in a similar fashion. The manifolds provide a structure to combine several functions required in the flushing, washing, or priming of microscale devices. For example, the manifold provides: a structure to receive solutions from reagent conduits; ring reservoirs for uniform, prompt, and low volume distribution of solutions; mesoscale channels to direct solutions to and from intended wells; a structure to mount control valves and receive valve activation energy; a structure to mount and route data communication lines between computer systems and data storage modules, transducers, and sensors; and/or, a mounting surface for proper alignment and contact of orifices with wells of microscale devices. The manifolds are typically laminated structures with a three dimensional system of internal solution reservoirs and channels arranged to quickly supply and remove solutions from microscale devices while reducing generation of waste.

Manifolds of the invention, e.g., as shown in FIG. 1, include layered manifold assembly 10 wherein solutions are fed from solution supply ports 11 to concentric ring reservoirs 12, and through mesoscale channels 13 to orifices 14 positioned to functionally align with wells of a microscale chip. The radial design provides numerous benefits, including, e.g., uniform path lengths between reservoirs and orifices, short path lengths between reservoirs and orifices, ability to share channel segments for delivery of more than one solution, and the possibility of individual controllable channels leading to each individual orifice. Uniform path lengths can provide uniform resistance to flow for consistent volume delivery and consistent solution supply times at each well. Short path lengths can reduce process cycling times and reduce waste of solutions. Sharing of channel segments can simplify control systems, simplify channel layout, and reduce solution waste. The ability to control solution flows individually to each well provides the flexibility to separately determine the type of solution to be delivered, the timing of delivery, the volume of delivery, and/or the like for each microscale device well to be processed.

Figure 2:
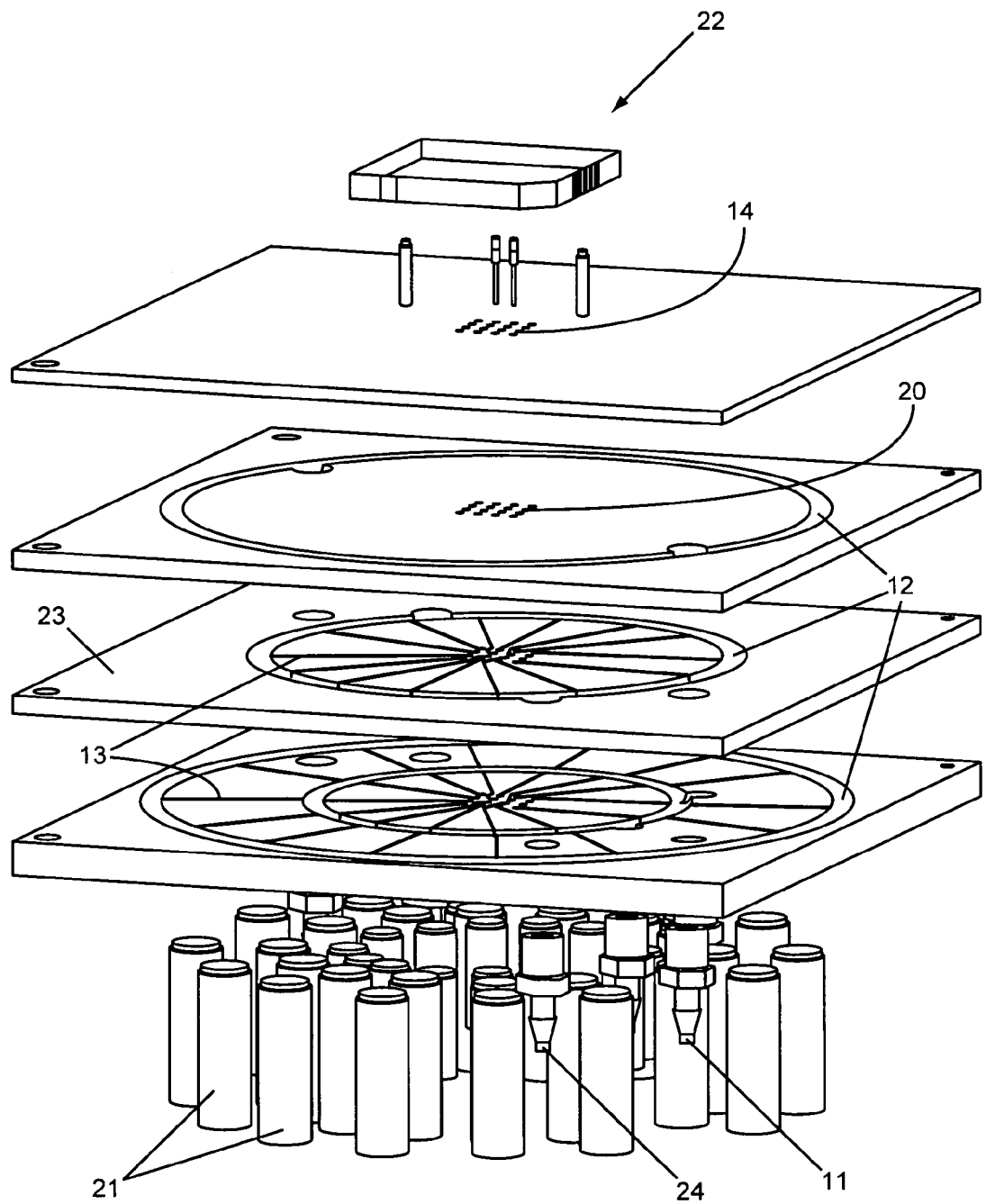
FIG. 2 is a schematic diagram of an expanded view of a layered three dimensional manifold.

The radial design can be practiced, e.g., by using three dimensional laminated manifold construction, as shown in FIG. 2. Ring reservoirs 12 can receive solutions or gasses from solution supply ports 11 which penetrate manifold layers at positions intersecting the ring reservoirs. Mesoscale channels 13 run in the plane of manifold layers and make fluid contact with connecting channels 20 to traverse other manifold layers, e.g., to terminate at orifices 14. Pneumatic actuators 21 can be mounted in an array at locations on the manifold corresponding to mesoscale channel segments carrying solutions from ring reservoirs. The pneumatic actuators can penetrate the manifold layers to power control valve mechanisms at points adjacent to the mesoscale channel segment. In this way, the flow of a solution from each ring reservoir through mesoscale channels to each orifice and microscale device 22 well can be controlled by application of gas pressures to the pneumatic actuators.

Figure 3:
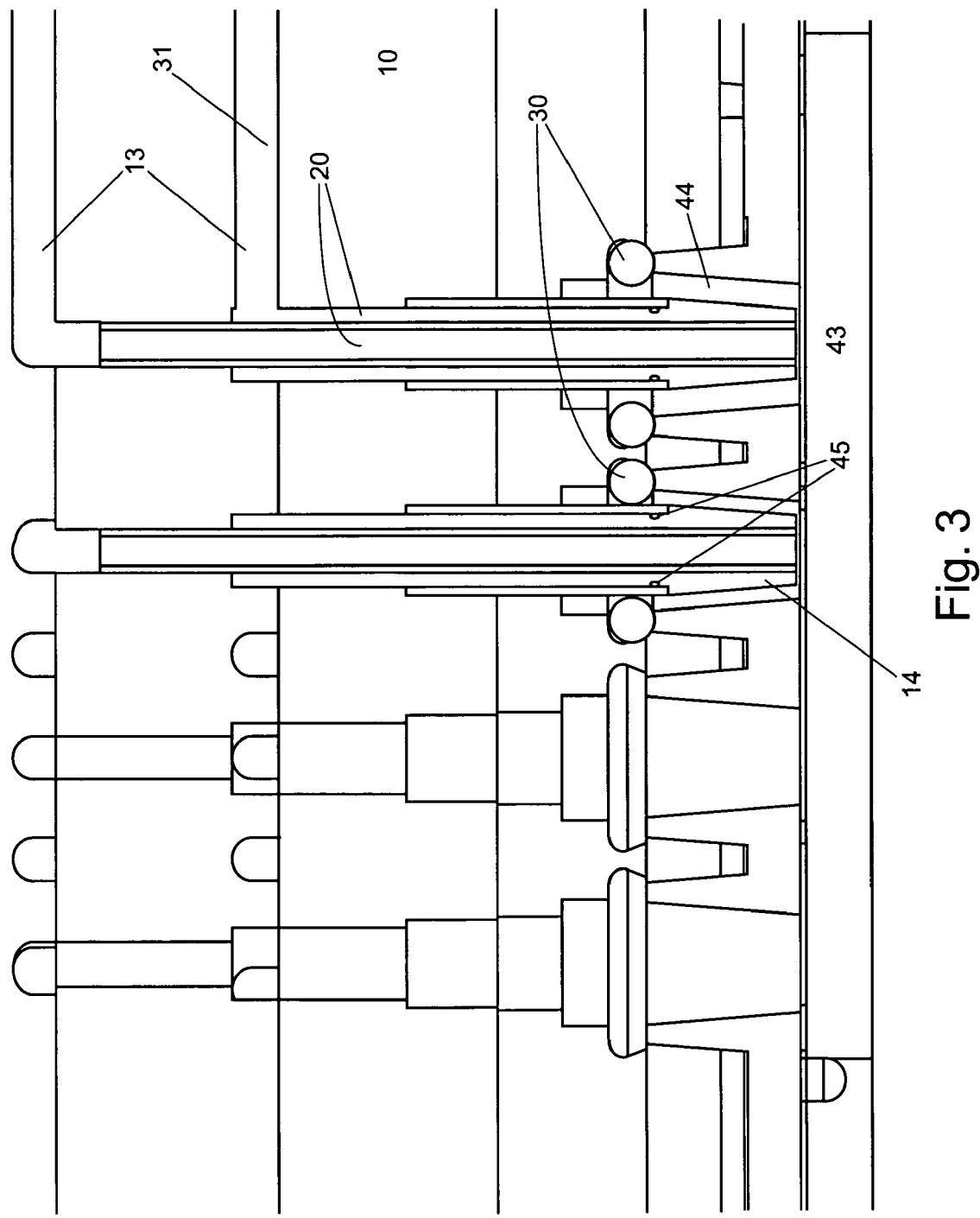
FIG. 3 is a schematic diagram depicting a cross sectional view of orifices of a manifold interfacing with wells of a microscale device.

Manifolds of the invention can carry waste solutions away from microscale device wells. For example, as shown in FIG. 2, mesoscale channels in waste solution removal manifold layer 23 can be fluidly coupled with the orifices at one end and to a ring reservoir associated with waste port 24. The waste port can be in fluid contact with a vacuum source to induce flows from the orifices to the waste solution ring reservoir. Orifices 14 can communicate with more than one mesoscale channel. For example, solution and waste connecting channel segments 20 can run side by side or concentrically to the orifice, as shown in FIG. 3.

Although solutions can be provided directly to a mesoscale channel or through reservoirs not in a ring design, the use of ring reservoirs is preferred in manifolds of the invention. If mesoscale channels were fed directly from a solution port, or from an eccentric reservoir, the flowpath lengths will typically vary significantly to reach different orifices. Different flowpath lengths can result in significantly different flowpath resistance, inconsistent delivery times, and different delivery volumes at different orifices. Efforts to provide uniform flowpath lengths without ring reservoirs often require serpentine or wayward channels that default to the longest flowpath length. Longer flowpath lengths can result in slower solution transitions and wasted solutions.

In one embodiment, ring reservoirs with different major diameters can be concentrically positioned in different layers of a manifold. The different diameters allow solution supply ports or waste ports to access the reservoirs through several manifold layers without contacting unintended reservoirs. Ring reservoirs with different diameters allow a self flushing progression of consecutive solutions through shared mesoscale channel segments. For example, a wash and prime sequence requiring three solutions can begin with process solution flowing through first mesoscale channels from an inner ring reservoir to wash wells of a microscale device. A rinse solution can flow through second mesoscale channels from an intermediate radius ring reservoir to intersect with and flush shared first mesoscale channel segments before rinsing the wells. Finally, a priming solution can flow through third mesoscale channels from an outer radius ring reservoir to intersect with and flush the shared second, then first, mesoscale channel segments before priming the wells. This sequence makes efficient use of the available mesoscale channels. This sequence flushes earlier buffers from the inner mesoscale channels to reduce waste of solutions, avoid stagnation of solutions in channel "dead legs", and reduces the possibility of reagent cross contamination during later operation of the manifold.

Control valves can be located, e.g., in the flowpath between ring reservoirs and orifices. Typically, control valves are located at points of contact between mesoscale channels and ring reservoirs. Control valves controlling flows from inner ring reservoirs are typically 3-way valves located at a common intersection of the inner ring reservoir, the mesoscale channel leaving the inner ring channel, and a mesoscale channel coming from an outer ring channel. The 3-way valve can be, e.g., normally open to flow from the inner ring reservoir and normally closed to flow in the mesoscale channel from the outer ring reservoir so that actuation of the valve changes flow from the inner ring reservoir to flow from the outer ring reservoir. Alternate functional valving configurations will be apparent to those skilled in the art. Control valves can be any valves appropriate to a particular system, such as, e.g., pneumatic valves, solenoid valves, needle valves, sandwich valves, diaphragm valves, slider valves, ball and seat valves, and/or the like. The valves can be powered (switched), e.g., manually, electrically, pneumatically, or hydraulically. In one embodiment, a computer interface electrically actuates a solenoid valve on a gas line to release a pressurized gas that actuates a pneumatic actuator associated with a control valve on the manifold to provide automated control of flow of solutions in the manifold. Optionally, mesoscale channel flows can be controlled directly by solenoid valves. Solutions or gasses can be directed to and from individual wells, or groups of wells, by actuating valves dedicated to control of flow to each individual orifice. Optionally, groups of wells with common solution or gas requirements can receive solutions from a group of orifices through mesoscale channels with flow controlled by a single solenoid valve or pneumatic valve.

Figure 4:
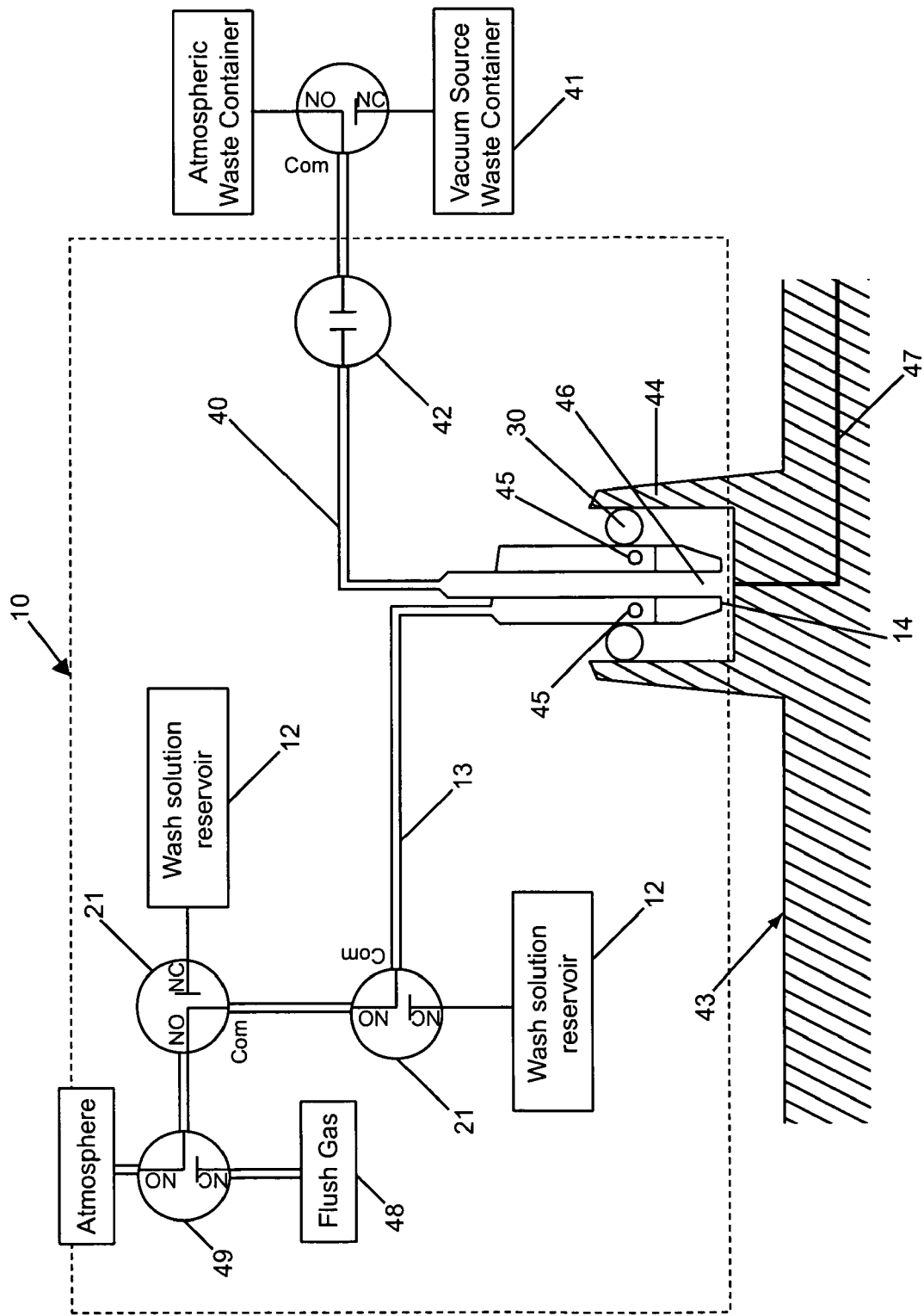
FIG. 4 is a schematic diagram of manifold configured to flush, wash, and/or prime, wells and/or microscale channels of a microscale device.

In some embodiments, a pressure differential can remove waste solutions from wells of microscale devices through mesoscale waste channels in the manifold. In one embodiment, as shown in FIG. 4, mesoscale waste channel 40 provides fluid contact between vacuum source waste container 41 and orifice 14 through waste control valve 42. The manifold can be operated to process microscale device 43 well 44 by flowing solutions from a solution reservoir 12 through mesoscale flush channel 13 out from the orifice through radial jets 45 to contact the walls of the well. As solutions flush through the well, they can be evacuated through waste channel 46 (concentric with the associated flush channel) of the orifice through the waste solution mesoscale channel to the vacuum source waste container. In some embodiments, a seal can be formed, e.g., by o-rings 30 positioned between the manifold 10 orifice 14 and the wells 44 of the microscale device 43 (also shown in FIG. 3). Pressurized solutions from the solution reservoirs can flow from the orifice jets, into the well and out the concentric waste channel to flush and wash the well. Optionally, a waste control valve can be closed to direct pressurized solutions or gasses into microscale channel thus washing or priming the microchannel.

In many embodiments that include gas flushing of manifold or microscale device components, control valves and channels can direct flow of a gas from a pressurized flush gas source. The manifold can be operated to flush solutions from mesoscale channels, wells, and/or microscale channels by directing flushing gasses along a flowpath having a pressure gradient. For example, as shown in FIG. 4, microscale device well 44 can be cleared of residual process solutions after a run of the device by creating a pressure differential between flush gas source 48 and vacuum source 41. For example, pressurized air can flow out from a gas source (typically having a pressure greater than atmospheric), through appropriately configured control valves, through flush channel 13 out from the orifice through radial jets 45 to contact the walls of the well and flush out residual solutions. The solutions and gasses can proceed through the orifice waste channel 46 through mesoscale waste channel 40 to be drawn into waste container 41 following a flowpath with a pressure differential having significant contributions from the vacuum source. In the configuration of FIG. 4, the flush gas can flush process solutions from mesoscale flush channel segments (shared with two or more process solutions), a well, a mesoscale waste channel, and optionally the microchannel. In other configurations, the flush gas can have a flowpath independent of process solution flowpaths, e.g., an independent ring reservoir, flush channel, orifice, and/or waste channel. Pressure differentials for flushing gasses can be provided between a pressurized gas source and an atmospheric vent, an atmospheric pressure source and a vacuum source, or between a pressurized source and a vacuum source. The pressure differential in the gas flush flow path can range from about 1 psi to about 500 psi, from about 10 psi to about 100 psi, or about 15 psi. A sealed contact between the orifice and well can allow continuation of a pressure differential between flush channels and waste channels. In one embodiment, residual process solutions are flushed from a well by atmospheric air (flush gas) flowing to the vacuum source, i.e., the solutions are sipped from the well by the vacuum source. In another embodiment, a jet of pressurized flush gas from the orifice ejects residual solutions out through the top of the well. In other embodiments, the orifice is sealed to the well and pressurized flush gasses are used to drive solutions from channels of the microfluidic device that are in fluid contact with the well.

Mesoscale channels typically run between reservoirs and manifold orifices. Mesoscale channels of the invention have a dimension, e.g., a diameter, width, and/or thickness, in the mesoscale range, e.g., from about 5 mm to about 0.1 mm, from about 1 mm to about 0.2 mm, or about 0.5 mm. The mesoscale range is useful to supply solutions or gasses to wells of microscale devices and to remove waste solutions from microscale devices in systems of the invention. Mesoscale channels have adequate capacity under commonly employed pressures to supply functional flush, wash, and prime flows over short time periods to wells and/or microscale channels of microscale devices. Larger channels can take up excessive space in the manifold and increase waste of solutions in many cases. Smaller channels can provide inadequate or unreliable solution flow rates in many cases.

Orifices on the manifolds of the invention interact with wells of microscale devices, e.g., to flush, wash, rinse, and/or prime elements of the device. Orifices can be, e.g., flush with the surface of a manifold or protrude to some extent from the manifold to functionally interact with the wells. When two or more orifices interact with two or more corresponding wells, the orifices can be spaced on the manifold surface to properly align for functional contact with the wells. In preferred embodiments, manifolds have 4 orifices, 8 orifices, about 16 orifices, about 34 orifices, or more. Arrays of orifices can be permanently arranged on manifolds to interact with corresponding arrays of wells on particular microscale devices, or orifices can have adjustable positions on the manifold to allow functional interactions with different arrangements of well arrays. Optionally, orifice arrays can be provided as interchangeable fixtures with orifice numbers and positions adapted to particular microscale devices and capable of fitting with desired fluid connections to a standardized manifold structure.

Orifices can be shaped to interact functionally with wells of particular microscale devices. Where the well is a simple access port flush with the surface of the microscale device, the orifice can present, e.g., a flat surface sealable, e.g., with an o-ring on contact with the well. More commonly, the well is a walled chamber with an open top on the upper surface of the microscale device. In this case, as shown, e.g., in FIG. 3, the orifice can protrude to fit with topography complimentary to surfaces of the well. For example a conical or hemispherical orifice can self-center and fit closely when inserted into a cylindrical, conical or hemispherical well, as is appreciated by those skilled in the art. Protruding orifices with tapered shapes are preferred embodiments, as they can aid in alignment and sealing of a manifold to a microscale device.

In a preferred embodiment, as shown in FIG. 3, tapered orifices can be sealed to tapered wells using resilient o-rings. Solution connecting channel 14 leads from solution mesoscale channel 31 to the well through jets 45. Solutions flowing from the jets can flow uniformly down through the space between the orifice and well wall to expel the well contents through the concentric waste connecting channel with a minimum of mixing. In a preferred embodiment, the jets form a radial array of perforations through the sides of the orifice.

Other System Utilities

Various utility subsystems can be employed to support the manifolds of the invention. Manifolds can require, e.g., pressure sources, vacuum sources, reagent sources, waste receptacles, physical mounts, and/or the like. During operation of the system of the invention, a sequence of flushing, washing, or priming steps can require, e.g., positioning of the manifold in functional alignment with the microscale device, a flow of wash solution, a flow of rinse solution, a flow of prime solution, removal of waste solutions, and/or removal of the manifold from contact with the microscale device.

Figure 8:
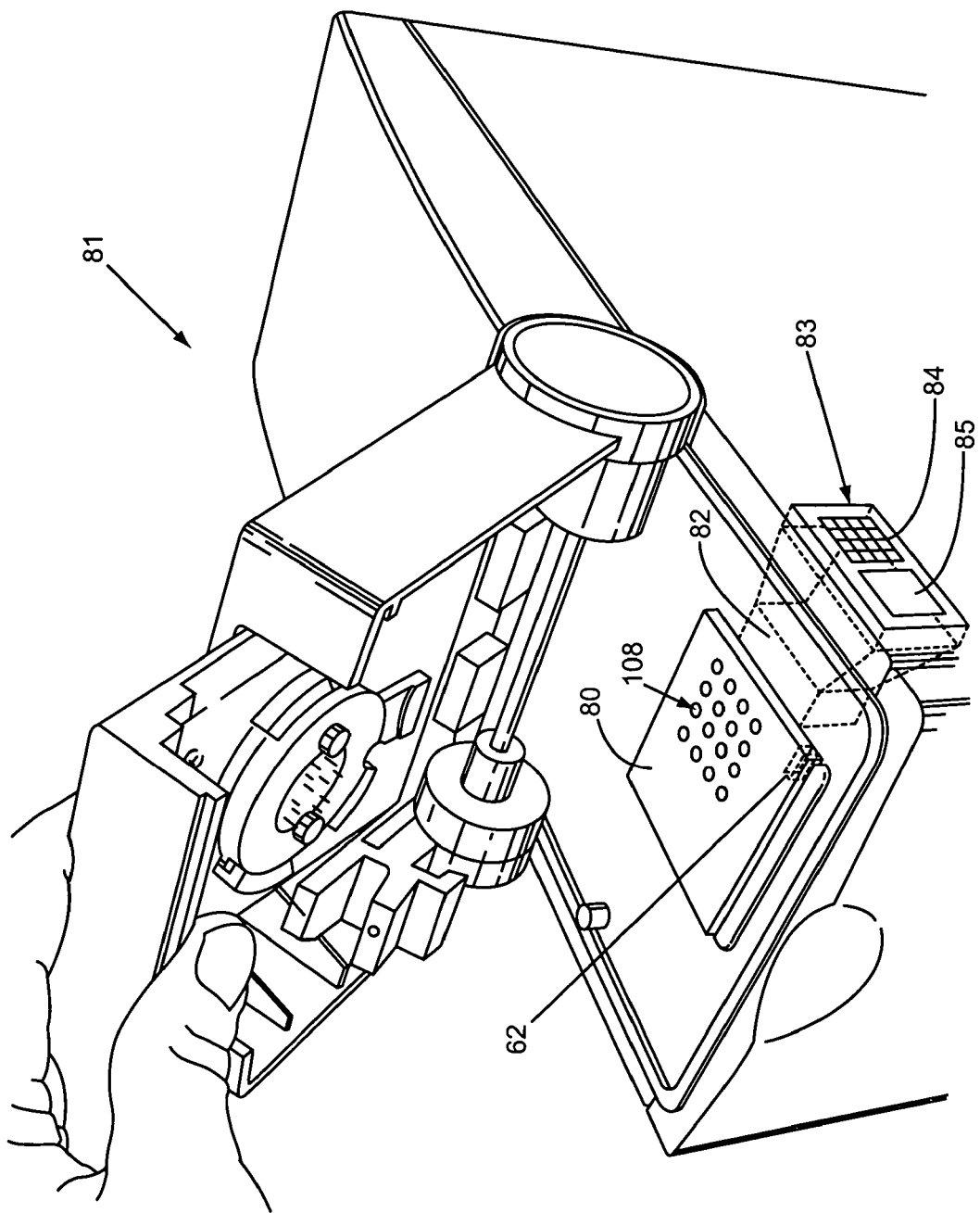
FIG. 8 is a schematic diagram of an apparatus including RFID read/write capabilities.

Manifolds of the invention can be positioned to functionally align and/or seal to the microscale device, e.g., manually, with guidance from a stage and pivot system, by a robotic system, and/or the like. For example, a technician can carry a microscale device to a system of the invention, align the wells with orifices of the system manifold, and press the orifices into contact with wells of the manifold. In a preferred embodiment, the manifold is an integral part of an instrument that contains all required utilities including an alignment and positioning mechanism (e.g., as shown in FIG. 8, or similar to the "folding down second physical unit 78" of published European application EP1360992, Apparatus for the Operation of a Microfluidic Device, by Berndt, M.) for consistent and precise alignment and contact between the manifold and microscale device. Alternately, a robotic system, e.g., of motorized articulated joints can position a manifold and a microscale device into functional alignment.

Figure 5:
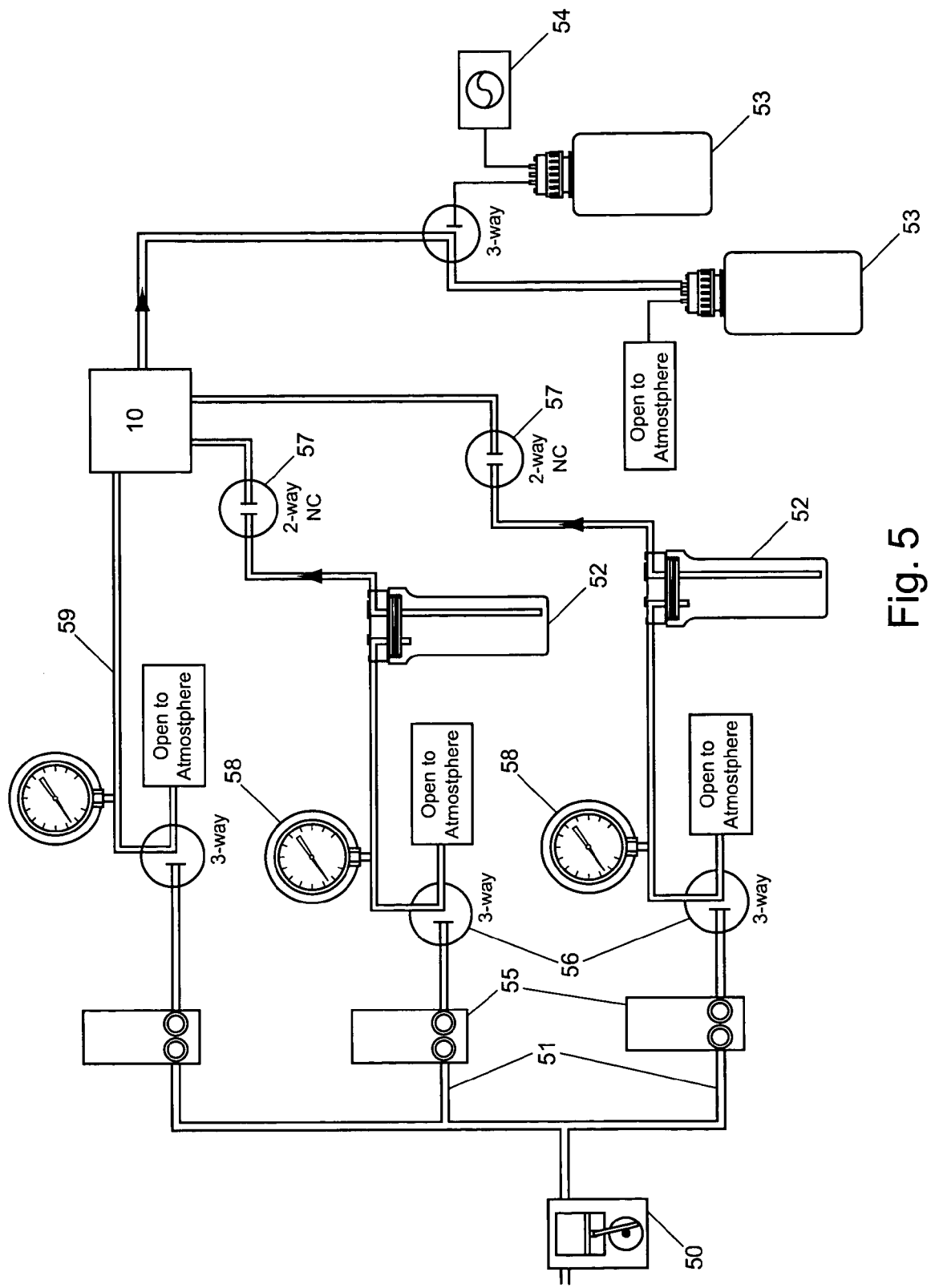
FIG. 5 is a schematic diagram of a processing system including support utilities.

Systems of the invention can include pressure sources to induce flows from reagent sources, as shown in FIG. 5. Pressurized gas can be supplied from an air pump 50 through gas lines 51 to reagent bottles 52. In one aspect of the systems, flushing gas flowpath 59 runs from a pressurized gas source through manifold 10 to, e.g., vacuum waste container 53. Process solutions, such as, e.g., wash solutions, rinse solutions, microscale device priming reagents, and/or the like, can be forced to flow from the reagent bottles along a pressure gradient in a flowpath through the manifold 10 and microscale device to waste containers 53. The pressure gradient inducing flow of waste solutions through the manifold to the waste containers can be supplied by a vacuum (relative low pressure) at the waste containers generated by vacuum pump 54.

Pressure regulation components of the system can be used beneficially to provide constant, accurate and repeatable pressures in the system to help obtain consistent solution flow times and flow volumes. Pressure regulation can be provided by, e.g., traditional spring loaded diaphragm based pressure regulators, or preferably by electronic gas pressure regulators 55, such as the Type 900 model regulators from ControlAir, Inc. of Amherst, New Hampshire. Manual or automatic pressure supply valves 56 and reagent supply valves 57 can be provided, e.g., to enable flows or isolate system components. Mechanical, electronic analog, or digital pressure gages 58 can be provided for technician readout or data acquisition in the system.

Flushing gasses can be provided, e.g., as compressed air from air pump 50, or optionally a pressurized tank of flushing gas. Tanks of gasses can have pressure regulators to provide the desired flushing gas pressure. Flushing gasses can be, e.g., air, nitrogen, inert gasses, carbon dioxide, sanitizing gasses, and/or the like. In one embodiment, one end of the flushing gas flowpath is open to atmosphere and the other end is a relative vacuum provided by vacuum pump 54.

Automated Systems

Although it is possible to control the system flows manually, automated system flow control is preferred. For example, a computer can send commands through a computer interface to actuate valves for control of solution flow routes, flow rates, and flow times. In a typical embodiment, a computer sends programmed valve position instructions through a communication interface that applies current to solenoid valves that control the flow of pressurized gasses which in turn change the position of pneumatic control valves controlling the flow of solutions in mesoscale channels.

Computers in systems of the invention can include, e.g., a programmed or programmable digital processor. For example, the computers can be a desk top personal computer, a lap top computer, a main frame computer, a processing unit with digital memory and a central processing unit, an electronically programmable read only memory, hard wired integrated circuits, and/or the like. The computers can be programmable and capable of communicating with other system components. The computer can, e.g., receive information from sensors, send timed instructions to electronic and mechanical components, evaluate conditions and provide adjustments to the system, track the progress of a process, and store process data. Systems in the present invention can include, e.g., a digital computer with data sets and instruction sets entered into a software system to practice the microscale device processing methods described herein. The computer can be, e.g., a PC (Intel x86 or Pentium chip compatible with DOS, OS2®, WINDOWS® operating systems), a MACINTOSH®, Power PC, or SUN® work station (compatible with a LINUX or UNIX operating system), or other commercially available computer which is known to one of skill. Software for receiving data and controlling processes is available, or can easily be constructed by one of skill using a standard programming language such as Visualbasic, Fortran, Basic, Java, or the like.

The computer can communicate with other system components, e.g., through a computer interface. The computer interface can, e.g., receive analog or digital signals from system sensors or keypads. The computer interface can, e.g., send digital or analog instructions, or apply power to mechanical actuators. For example, when the computer sends an instruction to open a valve, the interface can apply a voltage to an electric circuit that mechanically switches a valve. Computer interfaces are commonly available, such as those marketed by Optimux Controls of Coral Springs, Fla.

Data Storage modules

Data storage modules can be part of the microscale device processing system, e.g., to identify and track the history of particular microscale devices. Data storage modules can be mounted in or on the microscale devices so that, e.g., relevant information can be available and updated in real time. For example, data storage modules can provide: an event counter, chip identification data, chip usage data, sample analysis data, wash cycle data, a part number, a serial number, a work order number, or chip design number, calibration data, a manufacture date, an expiration date, a usage limit number, error codes, and/or the like associated with a device. In a preferred embodiment, a counter in the memory of a data storage module can be updated with every use cycle. Use of the microscale device can be discontinued when it has been used for a predetermined maximum number of cycles, e.g., after 2 cycles, 5 cycles, 10 cycles, 20 cycles, 40 cycles, 100 cycles, or more.

Figure 6:
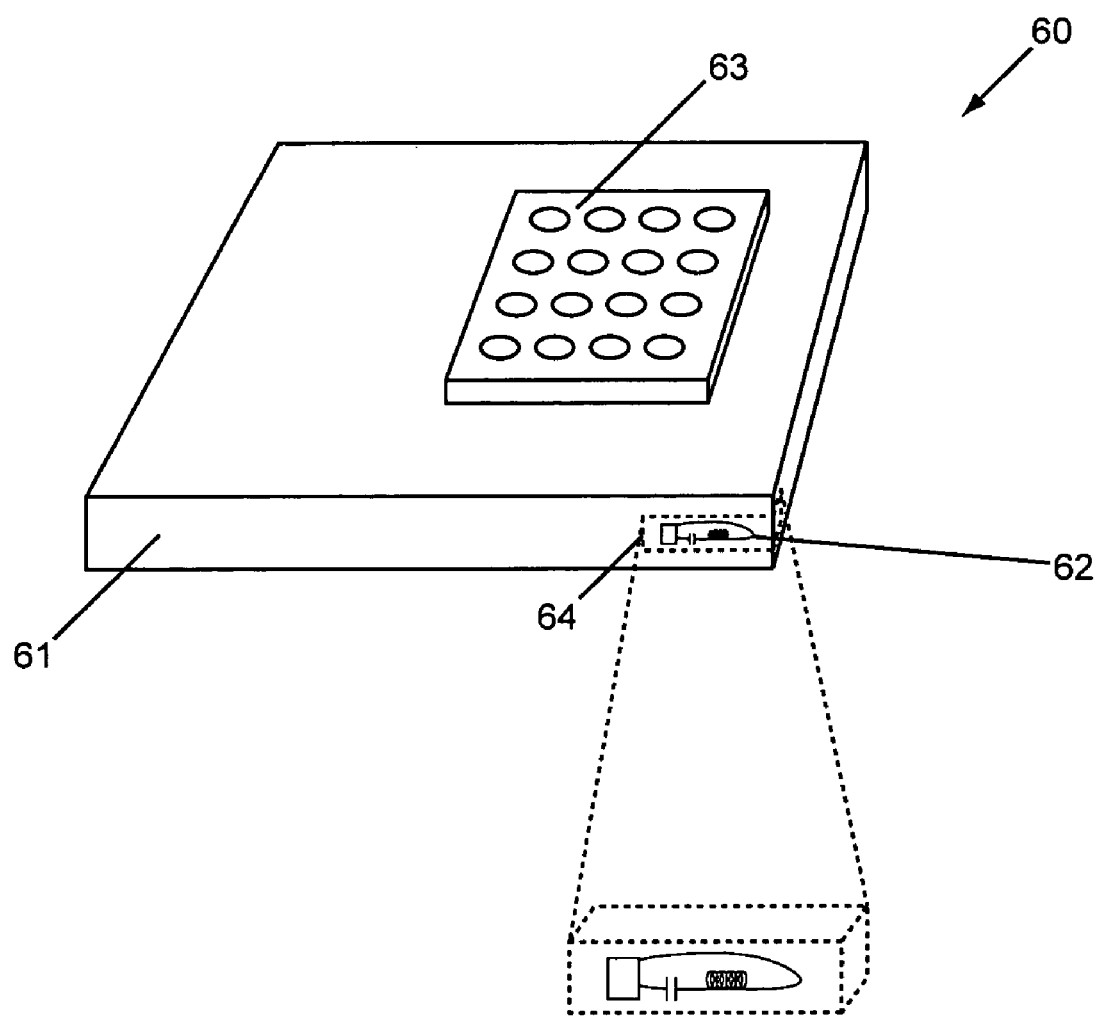
FIG. 6 is a schematic diagram of a microfluidic cartridge type of microscale device with an embedded data storage module.

Data storage units can be mounted to a microscale device, e.g., by incorporation into the microscale device, mounting onto the microscale device, mounting to a mounting plate of a microfluidic cartridge microscale device, and the like. In a typical embodiment, as shown in FIG. 6, a microfluidic cartridge microscale device 60 includes a mounting plate 61 that incorporates data storage module 62. The microfluidic cartridge includes a microfluidic chip 63 affixed to the mounting plate.

A mounting plate can be part of a microscale device that provides a framework for holding and handling components of the microscale device, such as, e.g., a microfluidic chip or data storage module. The mounting plate can be, e.g., a frame for: mounting a microscale device in a stable orientation; providing easy handling of a microscale device; providing well walls in fluid contact with microchannels of the microscale device; providing a sanitary and low particulate environment for a microscale device; providing pathways and connections for utilities such as electrical, optical, or pressurized fluids used in operation of a microscale device; providing mounting locations for accessory devices such as data storage modules and detector components; and/or the like. The mounting plate can be made from rigid, durable materials that protect relatively fragile chip 63 during handling of the microscale device. Thermoplastics such as acrylics, polyethylene, and polycarbonate are particularly well suited to the mounting plates of the present invention, although composite materials could also be used, such as fiberglass, carbon fiber, and other epoxy-based materials. Optionally, the mounting plate can be a part of a unitary structure including the microchip.

In one embodiment, as shown in FIG. 6, data storage module 62 is embedded in mounting plate 61. The mounting plate can be molded, e.g., in thermoplastic with a pocket 64 included for mounting a data storage module 62. The data storage module can be placed within the pocket, e.g., then permanently mounted using a polymerizable matrix, such as an epoxy resin. In another embodiment, the data storage module can be attached directly to the chip 63, e.g., in cases where the microscale device does not include a separate a mounting plate, or if it is otherwise desirable for the data storage module to be in close proximity to the chip.

Figure 7:
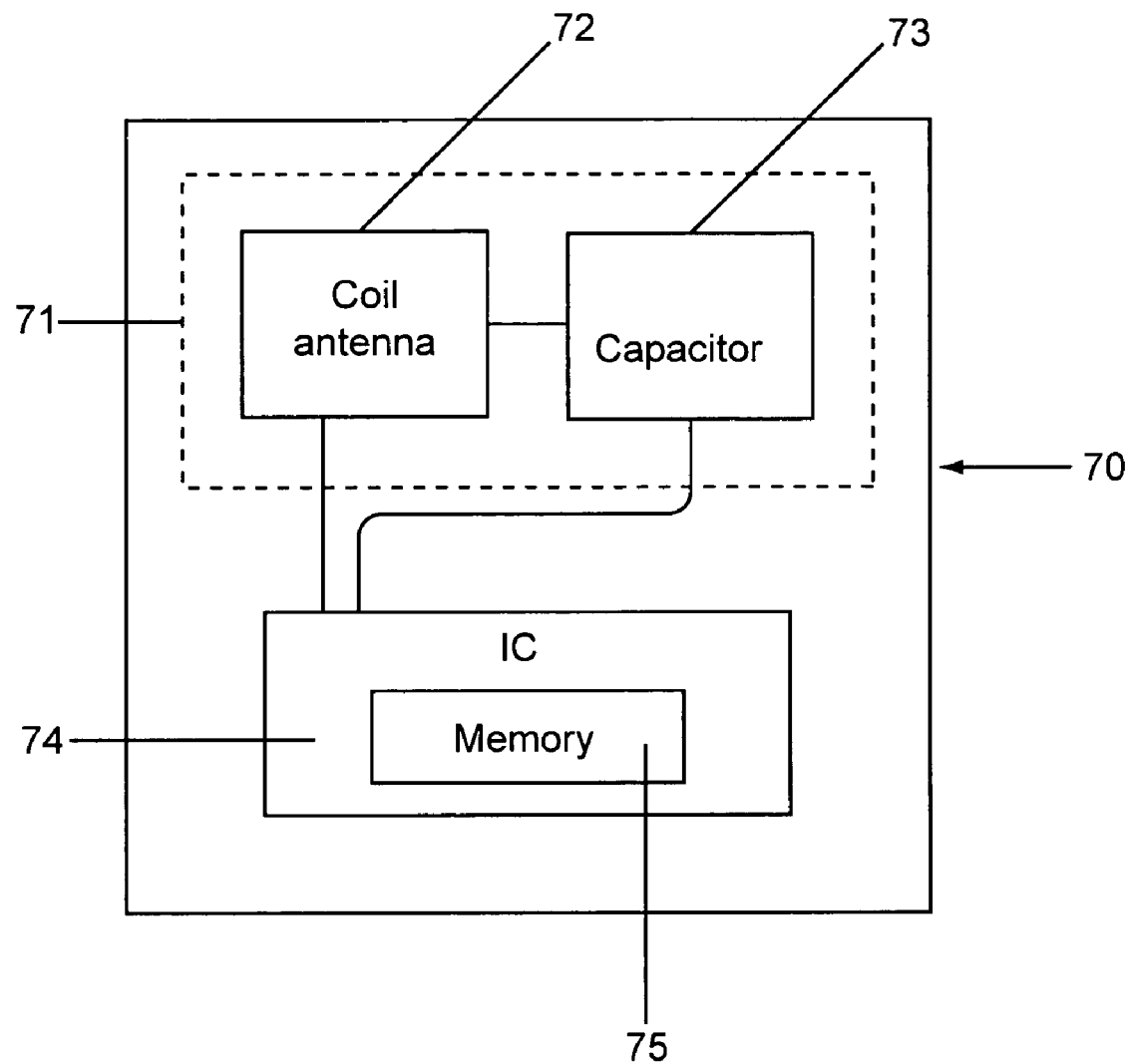
FIG. 7 is a schematic diagram of a radio frequency identification (RFID) tag.

In one embodiment, the data storage module is an RFID tag which allows information relevant to the microscale device to be read from and/or written to the tag. Referring to FIG. 7, a block diagram of a typical RFID tag is shown. RFID tag 70 can include a passive resonant radio frequency (RF) circuit 71. The RF circuit can be any suitable circuit known in the art, e.g., coil antenna 72 and capacitor 73 can form a resonant circuit with predetermined resonant frequencies. This RF circuit can play roles, e.g., in powering the RFID tag, transmitting signals, and/or receiving signals. The resonant frequencies of the RF circuits typically range from 125 kHz to 2.45 GHz. The RFHD tag can also include an integrated circuit 74 with a programmable memory 75, such as a 2048 bit or larger memory, for storing data. These components are typically assembled into a plastic package with, e.g., a segment of antenna 72 protruding outside the package. In a preferred embodiment, the RFID tag is placed on a perimeter of the microfluidic cartridge to allow adequate proximity to receiver or transmitter elements of associated RFID readers.

RFID technology is well-known, and RFID tags have been developed and are available off-the-shelf from a number of companies such as Philips Semiconductors, Motorola, Texas Instruments, and IBM. One example of such an RFID tag is the HITAG™ 1 Stick Transponder, Model No. HT1 DC20 S30, available from Philips Semiconductors, Sunnyvale, Calif. An RFID tag can be acquired from the manufacturer with a blank memory that has been formatted during manufacturing. Once the RFID reader has powered the RFID tag, information can be read from or written to the integrated circuit 74. Such information can include, e.g., calibration data for analysis, and/or statistics for use in satisfying regulatory requirements in certain industries.

The integrated circuit programmable memory can hold device identification codes and parameters associated with the device. For example, information stored in the IC can include: various chip identification information such as part number, serial number, a work order number, or chip design number; various calibration data as determined during manufacture; date of manufacture; chip expiration date; the maximum number of permitted analyses; a current count of analyses performed; the maximum number of washes allowed; a current count of completed wash cycles; an error code indicating a problem detected in the chip; and/or a cyclic redundancy check. Much of this data, such as, e.g., chip ID numbers and maximum cycle numbers, can be initially determined at the point of manufacture, and normally would not be altered during the life of microscale device. Other information, such as the number of analyses performed or the number of washes completed, can be incrementally, iteratively and automatically updated when appropriate.

Data storage modules and associated subsystems can be incorporated into microscale device reprocessing systems of the invention, as well as microfluidic analysis systems. Referring to FIG. 8, microscale device 80 can be used, e.g., in an instrument, such as analysis apparatus 81 which can provide utilities and detection devices that interact with the microscale device. One such apparatus that could employ the reprocessing systems and data storage modules of the invention is described in pending European Application No. EP 1360992, filed on Jun. 15, 2000, which is incorporated by reference herein in its entirety. Many such devices are available commercially, such as the Agilent 2100 BioAnalyzer, available from Agilent Technologies. For use with the data storage module of the present invention, analysis apparatus 81 can also include an RFID reader 82 integrated into the analysis apparatus, e.g., in close proximity to microscale device and associated RFID tag. Power for the RFID tag can be derived from the tag antenna (shown in FIG. 7) when a RFID reader is brought within a certain distance of the tag, typically approximately 5 mm or less.

Figure 9:
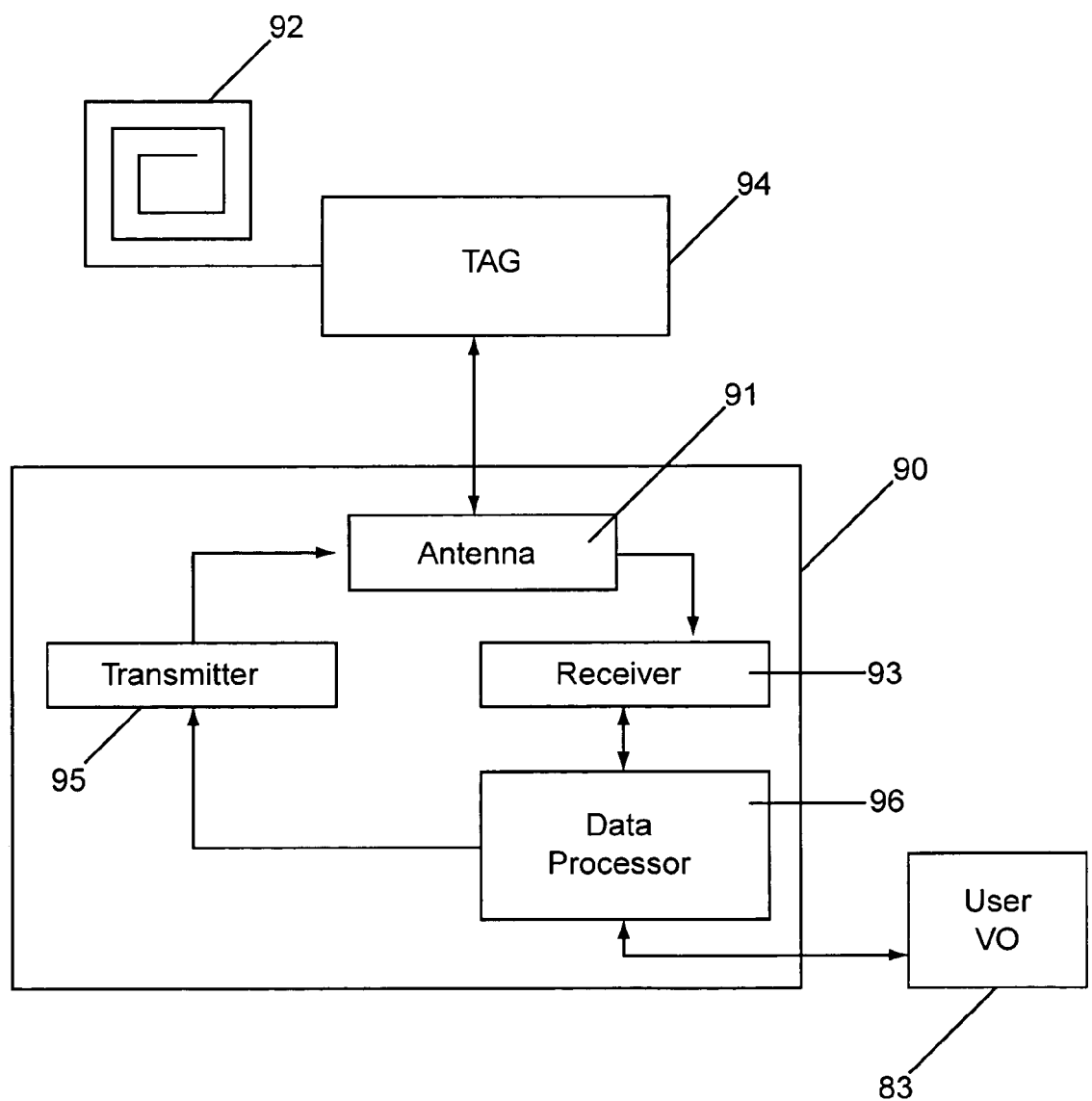
FIG. 9 is a schematic block diagram of a typical RFID tag:RFID reader system.

The tag reader, as shown in the block diagram of FIG. 9, can comprise RFID reader 90 with reader antenna 91 which can create an RF field that excites tag antenna 92 on the RFHD tag, causing RF circuit to resonate, as described above. The RFID reader can include, e.g., receiver 93 for reading information stored and transmitted from the RFID tag 94 as well as transmitter 95 to send signals to update information stored on the RFID tag. The RFJD reader can include data processor 96 including appropriate protocols for interpreting RFID tag signals and/or correctly transmitting information to update RHID tag stored parameters. The RFID reader can have a digital memory, e.g., for maintenance of an event log. The analysis apparatus 81 of FIG. 8, can include an input/output device 83 with keypad 84 or a touch-screen, so that a technician can manually input, e.g., an enabling password, data updates, and/or process instructions. The input/output device can include a display 85 to display information related to the apparatus and/or the microscale device. In some embodiments, an RFID reader can be incorporated into the microscale device, e.g., in the mounting plate, to assure appropriate proximity to the tag antenna. In such a case, communication contacts can be provided, e.g., to transfer information between the microscale cartridge and any associated apparatus. Optionally, the RFID reader can be a separate hand-held unit that a user can place in the proximity or the RFID tag to allow communications.

While RFID tags are particularly well-suited for the present invention, other devices can optionally act as data storage modules of the invention. For example, chip identification information and other information that does not change can be stored as unalterable readout using certain other coding mechanisms. For example, data can be stored in the form of mechanical keys, spring-loaded pins embedded into mounting plate, or protrusions molded into mounting plate or chip that fit into reading slots on the analysis apparatus. Bar code labels and laser-based bar code readers, which are well-known in the art, can provide data storage suitable to maintain unchanging information. In another embodiment, an EEPROM with programmable memory in an integrated circuit can be used as a data storage module capable of storing and updating information. Such an EEPROM data storage module would preferably be provided with a reliable power supply. In yet another embodiment, an optical read/write device, such as compact disc technology with laser readable/writeable reflective patterns can be integrated into the mounting plate of a microscale device. A laser disposed on the analysis apparatus could read or write information onto the optical storage device.

METHODS FOR PROCESSING MICROSCALE DEVICES

Microscale devices, such as microfluidic chips, often require a considerable amount of handling and preparation in association with analytical operations. This can include flushing process solutions over surfaces of the devices, e.g., preliminary flushing and washing of new chips, and flushing, washing, and priming of used chips. Such non-analytical processes can require inordinate time and effort if accomplished manually. The methods for reprocessing microscale devices described herein can significantly enhance the speed, efficiency, and reliability of microscale device cleaning, rinsing, and priming.

Before a microscale device is used or reused for analysis, it is typically washed to clear wells and channels, and to temper surfaces. Washing typically occurs, e.g., in two steps: a NaOH or sample buffer wash followed by a distilled water flush. The wash process solutions can be are flushed from wells and/or through microchannels by applying a vacuum or positive pressure to appropriate wells of the device. During the NaOH or sample buffer wash step in a typical procedure, the pressure and wash time combination can ensure, e.g., that at least 10 to 50 volumes are flushed through the various wells and channels of the microscale device. During a distilled water flush step, 5 to 30 volumes typically pass through the channels. It is desirable to complete the wash steps in about 400 seconds, or less. It is desirable to provide processing conditions that allow reliable reuse of the device for at least 30 use cycles. After wash processing, a technician is often required to load selective media and prime the device with buffers using manual injection methods. Time and effort can be saved, and reliability enhanced, using the processing methods described herein.

Washing a Microscale Device

Microscale devices can be processed before first use or reprocessed after a use. Wash processing generally includes flushing old fluids from the device, removing residue from device surfaces, and flushing the wash process solutions from the device. Washing a microscale device by methods of the invention is facilitated by the use of a manifold configured to, e.g., contact and seal to wells of the device to provide pressure induced flows of gasses or solutions across wells and/or microchannels of the device. For example, a manifold with mesoscale channels to orifices adapted to seal with the device can be positioned to functionally contact wells of the microscale device, and one or more process solutions or flushing gasses can be flushed across well surfaces and/or microchannel surfaces of the device.

Manifolds for washing microscale devices can include structures with mesoscale channels routing process solutions from solution sources, through ring reservoirs, through mesoscale channels, and out through orifices arranged to functionally contact the wells of the microscale devices. The manifolds can be, e.g., blocks or wafer-like structures with the mesoscale channels running in three dimensions to deliver the two or more process solutions in a timed sequence. In a preferred embodiment the manifold is manufactured in layers with elements laid out in a logical plan and with functional connections provided at surface contacts between the layers. For example, mesoscale channels and a ring reservoir for transport of a particular process solution can be located on one layer, while mesoscale channels and ring reservoirs for other process solutions can be located on other layers. Channels and reservoirs for returning waste solutions can exist in yet other layers of the manifold structure. Optionally, channels and reservoirs for transport of two or more solutions can be located on the same layer. Solutions can transit between layers of the manifold through connecting channels and solution source channels to functionally interconnect with other conduits of the manifold.

Manifolds can be manufactured by methods known in the art, such as mold injection, lost wax schemes, micro-machining, etching, photolithography, and/or the like. In one embodiment, the channels and rings can be laid out in the form of a transient material that is melted or dissolved after a permanent unlayered manifold structure has been formed around them. In a preferred embodiment, manifold layers are fabricated separately by mold injection or lithography, functionally stacked with proper alignment of interconnecting channels, and fused by application of, e.g., heat, adhesives, pressure, photoactivated resins, and/or the like.

Washing a microscale device with process solutions can include, e.g., flowing the solutions from reagent bottles to reservoirs through mesoscale channels and out orifices to flush wells and microchannels of the device. Controlling the flows can be by manual adjustment of pressures across channel segments and/or setting of valve positions. In a preferred embodiment, control of valves and pressures is automated using a computer interface interacting with mechanical actuators and/or sensors.

Residual storage or process solutions can optionally be flushed from manifolds, wells and microscale devices using flushing gasses. Flushing gasses can be any suitable gasses, such as, e.g., air, nitrogen, carbon dioxide, inert gasses, and the like. In a preferred embodiment, the flushing gas is compressed air. Flushing gasses can eject residual solutions from wells or drive them out through exit channels, such as, e.g., waste channels or microchannels. Flushing gasses can flow under the influence of a pressure differential ranging, e.g., from less than about 1 psi (pounds per square inch) to more than about 500 psi, from about 10 psi to about 100 psi, or about 15 psi.

Flushing gasses can clear residual process solutions from wells of microscale devices. For example, the well can be part of a flushing gas flowpath including mesoscale flush channels, mesoscale waste channels, microchannels, and/or the top opening of the well. In many applications, residual solutions are removed from a well by a flow of flushing gas from a mesoscale flush channel through an orifice. In some embodiments, residual solutions are removed from a well through a waste channel driven by a flushing gas at about atmospheric pressure in the well along a pressure gradient (differential) to a less than atmospheric pressure (vacuum) in fluid contact with the waste channel. In other embodiments, process solutions are flushed from wells by a pressurized flushing gas flowing in a flowpath from a mesoscale channel, through an orifice sealed to the well, and out a mesoscale waste channel in fluid contact with a vacuum source. In some embodiments, residual solutions can be ejected, e.g., out the top opening of the well by a jet of high pressure gas from a manifold. In yet other embodiments, solutions can be removed from wells by sealing and pressurizing the well with flushing gasses from a flush channel to drive the solutions into a microchannel of the microscale device. When driving solutions into microchannels, it is generally desirable to avoid introducing the flushing gas into the microchannel if a priming step will be required to remove the gas.

Flushing gasses can be used to clear process solutions from manifolds of the invention. For example, at the end of a process sequence of buffers flushing gasses can be used to clear mesoscale channels, and/or ring reservoirs, in preparation for introduction of new and/or different solutions. In embodiments where process solutions are introduced into radial mesoscale channels in order from inner to outer ring reservoirs, the all the common channel segments will typically contain the last solution of the process. In this situation, it can be desirable to flush the final solution with flushing gas from the common channel segments before priming with one or more earlier process solutions. In embodiments where it is desirable to change a process solution, such as an analyte specific reagent, between process runs, entire flow paths from reagent bottles, through reagent supply lines to ring manifolds, and/or mesoscale channels can be flushed, e.g., to make way for washing solutions or reagents specific to a different analyte. Solutions can be cleared from manifolds of the invention by displacement with flushing gasses along pressure gradient flowpaths independent of microscale devices, e.g., by ejecting the solutions from orifices not in contact with a device. Optionally, e.g., a microscale device well can be part of a flowpath including a pressurized gas source, a ring reservoir, a mesoscale flush channel, the well, a mesoscale waste channel, and a vacuum source, to clear the manifold along with the well.

Microchannels of microscale devices can be cleared of solutions using flushing gasses. As gasses are much less viscous than liquids, they can have advantages in flushing microchannels. Microchannels can be cleared using flushing gasses from flush channels and/or waste channels through an orifice sealed to a well in fluid contact with the microchannel. Optionally, the pressure differential flow path can include, e.g., a vacuum source sealed to a waste well of the microscale device.

In certain situations where obstructions have resulted in failure of a microscale device, methods of the invention can clear debris from device channels. In one embodiment, manifolds and cleaning solutions can clear a microscale device (chip) of debris. For example, the wells of the failed chip can be emptied, e.g., with flushing gasses from a manifold in contact with the chip wells. A pressure differential can be produced between the manifold and the chip waste well to drive a 1% Hellmanex II solution into the chip of for a period of 30 minutes. The solution can be removed from the wells with another gas flush before flushing the wells and microchannels with a storage buffer for four minutes. Finally, the chip can be primed with selective gel media as usual in preparation for an analytical run.

Contacting microscale device wells with manifold orifices for processing can include, e.g., orienting the manifold so the orifices are aligned with wells on the microscale device and positioning the orifices in functional contact with the wells. Functional contact can include, e.g., inserting the orifices into the wells so that radial jets can rinse the well walls, positioning an orifice close enough to a well for solution transfer to take place, contacting a tapered outer orifice wall with an upper well surface or complimentarily tapered inner well wall, sealing the interface between the orifice and well with an o-ring, and/or the like. Functional contact can include an arrangement that provides desired flows of solutions between the orifices and wells regardless of any actual physical contact. In a preferred embodiment, the orifices are hydraulically sealed to the wells, e.g., so that hydraulic or hydrostatic pressures can be transmitted between them. For example, washing microchannels of the microscale device can be accomplished by sealing an orifice to a well in fluid contact with the microchannel, applying a pressurized source of wash solution to the well from the orifice, and closing valves in any mesoscale waste channel outlets, thus forcing the wash solution to flow into the microscale channel. Sealing the orifices to the wells can beneficially prevent drying of solutions or overflow of solutions from the wells. Optionally, orifices can functionally contact wells without hydraulic sealing, e.g., where the waste channel vacuum and capacity are adequate to prevent overflows, where the precision of flow control is adequate to prevent overflows, where overflow is desired in a flushing or washing process, where microchannel flows are induced by a relative vacuum at a microchannel outlet instead of by well pressures, and/or the like.

Washing a microscale device can include, e.g., flowing a sequence of process solutions through mesoscale channels of a manifold and well or microchannel surfaces of the microscale device. The sequence can include flowing process solutions at times and with volumes suitable, e.g., to flush old solutions from the device, remove residues accumulated during analyses, flush strong wash solutions from the device, and condition the device for receipt of fresh reagents and samples. Flowing the process solutions can be induced and controlled, e.g., as follows: prepared process solutions can be placed in pressurized reagent bottles with fluid contact through siphon tubes to solution supply ports, the pressures influencing the rate of solution flows; the solutions can flow under pressure to dedicated ring reservoirs; flow control valves located anywhere in the solution supply flowpath (preferably in mesoscale channels or at intersections of mesoscale channels) can direct the flow of each process solution through mesoscale channels toward orifices located central to the ring reservoirs, with the selection of open valves controlling the order of process solution delivery, and the duration of valve openings influencing the amount of process solution flowing through the channels; the process solutions can flow into a chamber created by sealing an orifice to a well; the process solution can flush the well, flow out of the chamber through a waste mesoscale channel, and/or flow into a microscale channel in fluid contact with the well. A sequence of process solutions can progress, e.g., from inner ring reservoirs to outer ring reservoirs or from outer ring reservoirs to inner ring reservoirs to prevent out of sequence release of trapped solution dead legs. The time required to process a microscale device can depend, e.g., on the process solution compositions, flow inducing pressure differentials, flowpath channel cross-section areas, flow control timing, and/or the like. In preferred embodiments, systems and methods are configured to provide flows adequate to process a microscale device in about 1000 seconds, about 500 seconds, about 400 seconds, about 200 seconds, about 60 seconds, or less.

Flowing process solutions in a sequence can provide cleaning and/or preparation of the microscale device for reuse or storage. For example, a washing process can include: flushing the microscale device with water or a buffer to remove remaining samples or reagents; flowing a wash solution, such as a surfactant solution or NaOH solution into the microscale device to strip residue from well surfaces or microchannel surfaces; rinsing the microscale device with water or a conditioning solution; flowing a storage solution, and/or flowing a priming solution into the wells and microchannels of the microscale device. In a preferred embodiment, the cleaning sequence is complete in 400 seconds or less. Storage solutions can include, e.g., 0.1 N NaOH, 20% ethanol, azide solutions, and the like. Priming solutions can include, e.g., neutralizing buffers, conditioning buffers, selective media, assay buffers, and the like.

In an aspect of the invention, process solutions in wells can be retrieved into the manifold, e.g., to reduce the consumption of reagents. For example, in cases where processing solutions are expensive to consume or dispose of, excess solution remaining in microscale device wells can be transferred into the manifold for use in a later processing run. The process solutions can flow under pressure from the well through an orifice, through mesoscale channels to a ring reservoir where they can be held until they are required in a future process. In a preferred embodiment, a relative low pressure is applied to a ring reservoir and control valves are configured to return a reagent to the appropriate reservoir for use future use.

In another aspect of the invention, process solutions can be conserved by not flushing them from microscale device wells while other wells and channels experience flushes, washes, etc, of a reprocessing sequence. In this way, expensive reagents, such as, e.g., difficult to obtain antibodies or recombinant proteins, can be retained in the same reagent well until the next use of the device. In a preferred embodiment, a low pressure is applied to the retained reagent well to provide a slow flow rate during washing of the other wells so that back flows from the other wells do not intrude back through microchannels to contaminate the retained reagent.

Figure 10A:
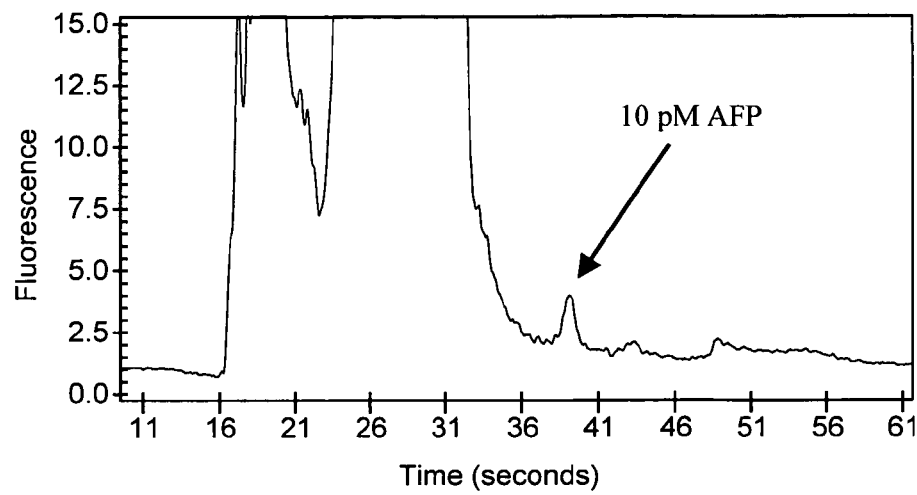
FIG. 10 is a series of charts showing the lack of significant carryover and repeatability of assay results after 30 uses and washes of a microscale device.
Figure 10B:
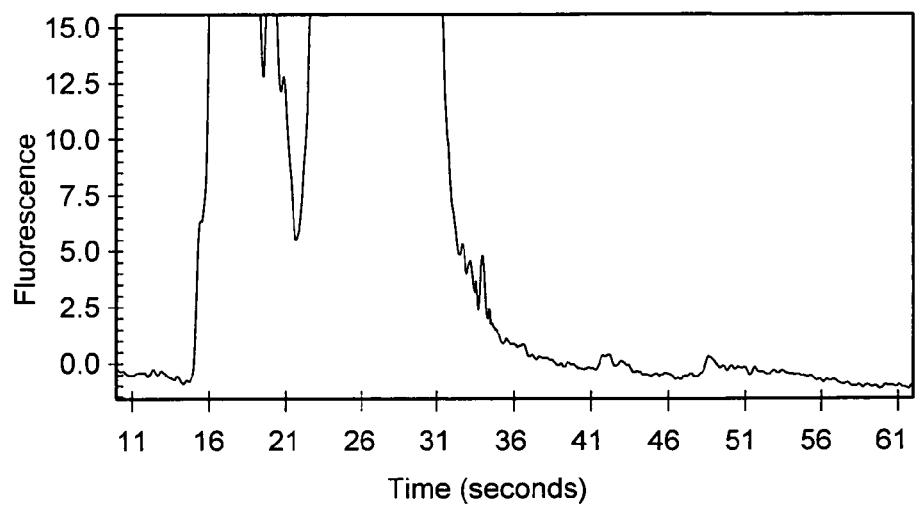
Figure 10C:
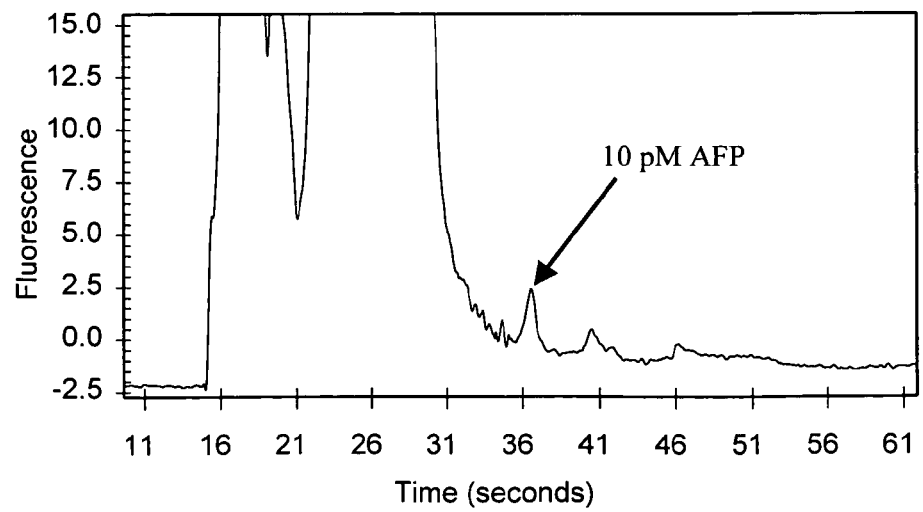

Washing microscale devices by methods of the invention can allow repeated reliable reuse of the devices without significant carry over between runs. For example, in one experiment shown in FIG. 10, a microscale device for alpha feto protein (AFP) analysis was used and washed 30 times with a sequence of 1N NaOH, followed by deionized water after each assay. FIG. 10A shows the initial AFP run detecting 10 pM of AFP. FIG. 10B shows the chart for a blank sample after 30 washes with no significant AFP carry over detected. FIG. 10C shows the result of the 30th AFP sample run with no significant degradation of the AFP signal. It is an aspect of the invention that sample analytes can be removed from the wells or microscale channels by a factor of a million or to less than 1 ppm.

Automated Controlling

Methods of processing microscale devices of the invention can include controlling processes with, e.g., digital logic devices, such as computers. Processing steps, such as, e.g., positioning manifolds on microscale devices, and controlling process solution flows, can be automated using the systems described above in the Automated Systems section above. Data handling aspects of the methods can be carried out with automated systems.

Contacting wells with orifices can be automated. For example, a technician can input instructions to a computer through a keyboard. The computer can activate robotic systems or other mechanical actuators to receive a microscale device, align it with a manifold, and bring orifices in contact with wells. Information about the identity and status or the microscale device can be read, e.g., from a data storage module coupled to the microscale device.

Flowing of process solutions can be under the control of automated systems. For example, software can be written to functionally coordinate interactions between a computer interface and mechanical actuators controlling manifold valve positions and pressure differentials. A timed sequence of pressurizations and valve openings can provide flushing gasses or process solutions in order, at flow rates, in volumes, for time periods determined by the software, as can be appreciated by those skilled in the art. Processing methods can be completed and repeated automatically without intervention by a technician.

Retaining and updating information about processes and particular microscale devices can help ensure the reliability of processing methods of the invention. Reading and writing information to data storage modules coupled to microscale devices can allow tracking and a history for trend analyses.

For example, when a particular microscale device, e.g., having a cartridge with a mounted data storage module, is positioned in an apparatus for processing, a data reader can read the identity of the microscale device along with other information, such as process cycle history. The data reader, in communication with a computer database, can update a file history on the particular microscale device and determine appropriate actions. The identification can indicate the type of manifold, process solutions, flow rates, flow sequences, and the like, appropriate to processing the microscale device. The file history for the device can provide quality control information indicating the current reliability of the device or provide total cycles data indicating the predetermined uses remaining for the device.

Reading from and writing to data storage modules, can depend on the type of device. Data storage modules with physically encoded information usually require physical contact with the data reader to transmit information. This is usually accomplished when the microscale device is being placed, e.g., on a stage associated with the processing system. More typically, bar codes or RFID signals are received when a microscale device with a data storage module is placed in proximity to the reader. In a simple embodiment, the reader receives identification information from the data storage module and stores it in a computer database. If the computer database indicates the microscale device has reached a maximum usage limit, further processing can be terminated or a notification displayed to a technician so the device can be disposed of. More sophisticated data storage modules, such as certain RFID tags, can receive information as signals transmitted from the reader. For example, the data storage module can be instructed by the reader to increase stored cycle counts, or add a sample identification to an assay history data base.

Data storage modules, such as electronic devices, can be powered by external sources or by dedicated sources mounted with the devices. Data storage modules with volatile memories can be provided with batteries to keep them energized. External power can be provided by illuminating an associated photovoltaic cell, e.g., with light from a reader; by providing electrical currents through electric contacts with the processing system; or by transmitting appropriate RF energy to RF circuits of a RFID tag.

EXAMPLES

The following examples are offered to illustrate, but not to limit the claimed invention.

Example 1

A Microfluidic Cartridge Reprocessing System

In this example, a stand alone processing system includes: a personal computer interacting with air pressure controllers and solenoid valves through a digital I/O interface; pressurized reagent bottles (containers) connected to the air pressure controllers and feeding solutions to ring reservoirs of a manifold through solution supply ports and solution supply control valves; the solenoid valves controlling the flow of house pressurized air to pneumatic valves operatively mounted to the manifold; and, solutions flowing from the ring reservoirs through mesoscale channels in the manifold past open pneumatic valves to orifices arrayed on the surface of the manifold.

The manifold is mounted on a swing arm above a stage adapted to hold a microscale device in a predetermined orientation. The microscale device is a microfluidic cartridge including a RFID tag data storage module mounted in a mounting plate. After the cartridge is placed on the stage, the manifold is swung down to precisely make functional contact between 14 manifold orifices and 14 corresponding microfluidic chip wells. A data reader mounted to the stage in proximity to the RFID tag in the cartridge transmits electromagnetic energy to the RF circuit to energize the tag. The energized tag transmits identity data and current usage counts data to the reader for communication to the computer.

The computer confirms that the usage count is not beyond the established maximum for that type of cartridge and initiates an appropriate processing sequence:

1) Through the I/O interface, the computer commands: pressurization of the reagent bottles by the air pressure controllers, opening of a first solenoid valve releasing pressurized air to open 14 pneumatic valves on mesoscale flush channels leading from an outer ring reservoir of 1 N NaOH to radial jets at of each of the 14 orifices in o-ring sealed contact with the chip wells; opening a solenoid valve releasing pressurized air to open 14 pneumatic valves on mesoscale waste channels leading from the center of each orifice to a waste ring reservoir under vacuum pressure. In this system configuration, 1 N NaOH flows along a pressure gradient from a reagent bottle, through a ring reservoir, through mesoscale flush channels, through radial jets directed high on the walls of the wells, and to the bottom of the wells where it is drawn up the mesoscale waste channels, through the waste ring reservoir and ultimately to a waste bottle under vacuum outside the manifold.

2) After a predetermined flow of NaOH has flushed old solutions from the well, the pneumatic valves controlling the mesoscale waste channels are closed, except the valve controlling flows from a waste well, to force the NaOH flow into microscale channels associated with the other wells. The NaOH flow flushes sample solutions, reagent solutions, and selective media from the microchannels, and chemically removes any residue from the previous run from the microchannel surfaces. The NaOH continues flowing from the microscale channels to a common chip waste channel, and to the waste well where it is removed through the one mesoscale waste channel remaining open.

3) After a predetermined flow and time with NaOH, the computer commands closing of the first solenoid valve to close the 14 pneumatic valves on mesoscale flush channels leading from an outer ring reservoir, and opening of a second solenoid valve releasing pressurized air to open another set of 14 pneumatic valves on the mesoscale flush channels leading from an inner ring reservoir of deionized water. Pneumatic valves on mesoscale waste channels remain open. The flow of 1 N NaOH stops and a flow of deionized water flushes the NaOH from common mesoscale flush channel segments, through the radial jets, through the wells, and out through the mesoscale waste channels to the waste ring reservoir. After a flow and time adequate to flush the NaOH from the wells, the waste flowpaths are configured to force the flush water into the microscale channels of the chip and out through the waste well.

4) The reagent bottles are depressurized by a computer command that opens vent valves on conduit between the air pressure controllers and the bottles. The manifold is swung up away from contact with the microfluidic cartridge, and the cartridge is removed for further use.

Example 2

Reuse of a Microscale Device

Figure 11:
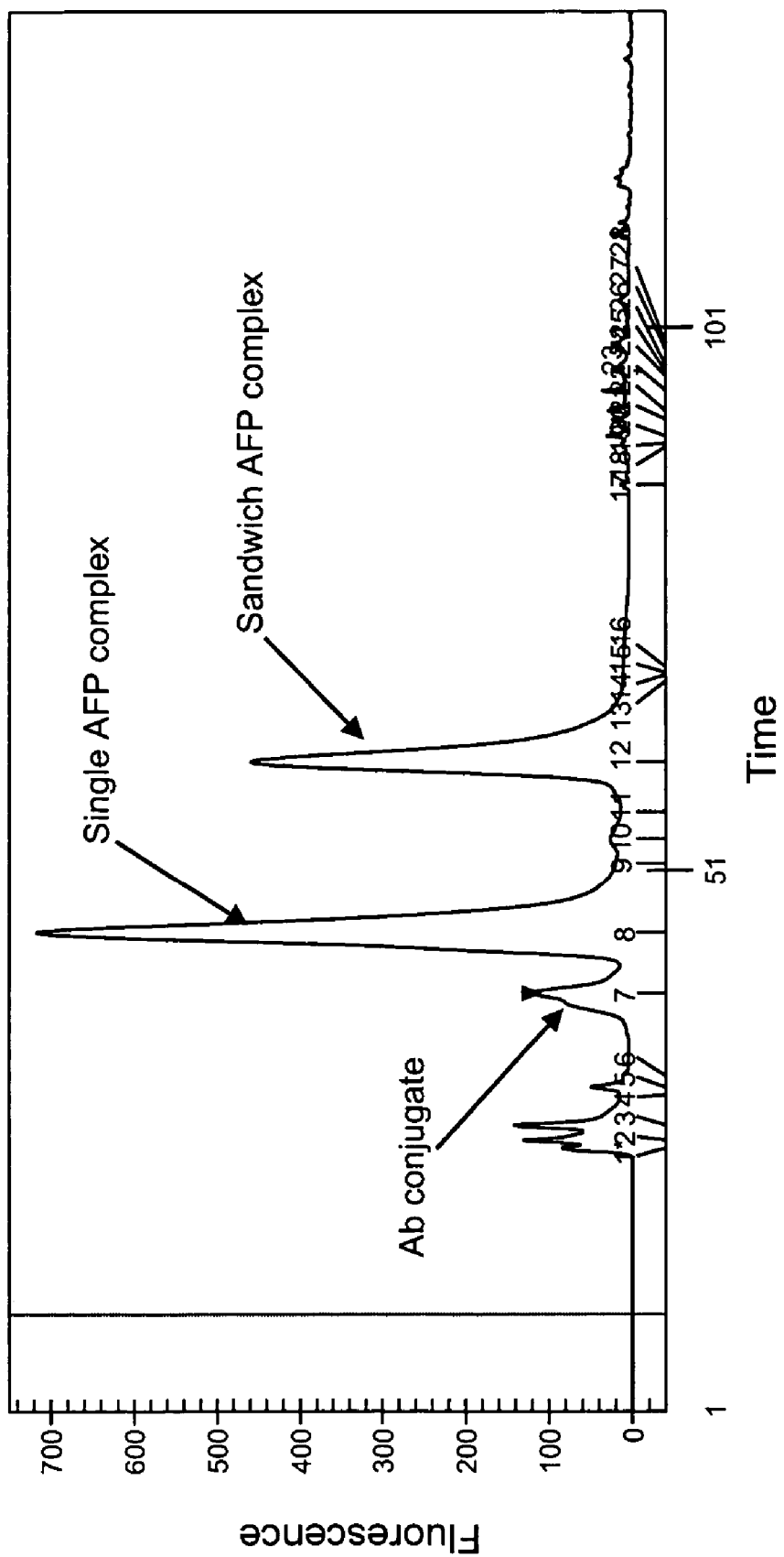
FIG. 11 is an electropherogram of an alpha-feto protein (AFP) assay carried out on a microscale device.

Repeated AFP analyses were run on the same sample repeatedly using the same microfluidic cartridge after washing with a processing system (washing fixture) of the invention. The AFP analysis is a liquid phase binding alpha-fetoprotein (AFP) assay involving reaction and binding on-chip of AFP to two antibodies (WA-1 and IgG) which bind to different sites of the protein. The WA-1 antibody is conjugated to a DNA molecule that carries fluorescent labels (Alexa) for the detection. The different complexes and products of the reaction are separated under the influence of an electric field in a separation channel that contains a polymeric matrix (size selective media), and appear at a detector at different times based on their mobility. A typical electropherogram of the assay in 10% serum conditions is shown in FIG. 11.

The method of the experiment is briefly outlined, as follows:
1) Fill the cartridge chip on washing fixture with 1N NaOH to wash all wells including a 9 minute pressurizing time to flush microchannels.
2) Fill chip on the washing fixture with H2O to flush all wells.
3) Run the first 10 pM AFP assay. No serum, regular selective media gel with no LCA or heparin.
4) Chip flushing with H2O on the washing fixture.
5) Run 1 uM AFP in 10% serum assay using gel with LCA+ heparin for the assay.
6) Chip washing by 1N NaOH on the washing fixture.
7) Flush waste well line twice with H2O.
8) Flush wells and microscale channels with H2O on the washing fixture.
9) Repeat step 5 to 8 four times, thereby running 5 consecutive 1 uM AFP assays in 10% serum on the chip followed by washes.
10) Check for carry-over after 5 times running the high concentration AFP and washing the chip. That is, run "blank", no serum, no AFP sample with conjugate on regular gel with no LCA or heparin.
11) Chip washing with H2O on the washing fixture.
12) Run 10 pM AFP assay (no serum conditions) to check for assay performance on chip after washing it. Use regular gel with no LCA or heparin.
13) Chip washing with H2O on the washing fixture.
14) Repeat steps 5-13 for a total of 30 assays and 6 blank runs.

Assay data were accumulated through 30 AFP assay runs (6 sets of 5 runs separated by running of carry over test blanks). Analysis results and parameters remained stable over the course of the 30 assay runs. For example, AFP sandwich complex migration times had a coefficient of variation (CV) was less than 2%, a peak height CV about 13%, and a peak area CV about 14%, excluding outlier sample 28. Quantitative results for actual assays would have been significantly more precise due to the normalizing effects of assay references. Performance of the chip was higher for other peaks, such as the AFP single complex peak with a migration time coefficient of variation (CV) was 2%, a peak height CV about 3%, and a peak area CV about 3%, excluding outlier sample 28.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be configured used in various functional combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A system for processing a microscale device, the system comprising:
    a manifold comprising a plurality of ring reservoirs in fluid contact with one or more mesoscale flush channels or one or more mesoscale waste channels, wherein two or more of the plurality of ring reservoirs are concentric and share a flowpath in one or more channel segments;
    one or more orifices in fluid contact with the flush channels or waste channels, and adapted to functionally contact one or more wells of the microscale device; and,
    one or more process solutions in a flowpath comprising the one or more mesoscale channels, the one or more orifices, and the one or more wells of the microscale device.

2. The system of claim 1, wherein the microscale device comprises one or more microchannels in fluid contact with the one or more wells, and wherein the flowpath further comprises the one or more microchannels.

3. The system of claim 2, further comprising one or more control valves in the one or more waste channels that can direct the one or more process solutions into the one or more microchannels.

4. The system of claim 1, wherein the mesoscale channels comprise a dimension ranging from about 5 mm to about 0.1 mm.

5. The system of claim 1, wherein the flush channels and waste channels compromise one or more concentric segments.

6. The system of claim 1, wherein the flush channels or waste channels comprise a pressure differential.

7. The system of claim 1, wherein the one or more process solutions comprise: NaOH, water, a reagent, a surfactant, a solvent, or a heated solution.

8. The system of claim 1, wherein the one or more process solutions comprise a wash solution comprising an alkaline solution of an ampholytic surfactant and chelator.

9. The system of claim 1, wherein the adapted orifices comprise: o-rings, a tapered surface, or both.

10. The system of claim 1, wherein the wells comprise: sample wells, reagent wells, waste wells, or a combination thereof.

11. The system of claim 1, wherein the orifices comprise one or more radial jets.

12. The system of claim 1, further comprising one or more reagent containers in fluid contact with the one or more ring reservoirs through solution supply ports.

13. The system of claim 1, wherein the manifold further comprises a multilayer structure.

14. The system of claim 1, wherein the manifold further comprises one or more control valves functionally associated with the flush channels or waste channels.

15. The system of claim 14, wherein one of the one or more control valves controls flow of the process solutions or a flushing gas to: one of the one or more wells, two or more of the one or more wells, or one or more groups of wells.

16. The system of claim 15, wherein the groups of wells comprise: sample wells, reagent wells, wash wells, or waste wells.

17. The system of claim 14, wherein the one or more control valves comprise: pneumatic valves, solenoid valves, needle valves, sandwich valves, diaphragm valves, slider valves, or ball and seat valves.

18. The system of claim 1, further comprising an automated flow controller.

19. The system of claim 18, wherein the automated flow controller comprises: a computer, an interface, solenoid valves, pneumatic valves, or an electronic pressure regulator.

20. The system of claim 1, further comprising a flushing gas in the flowpath.

21. The system of claim 1, further comprising a system configuration as an independent instrument or as a component of an analytical instrument.

22. The system of claim 1, further comprising a data storage module mounted to the microscale device.

23. The system of claim 1, wherein the process solution comprises a reagent to condition or prime the one or more wells or one or more microchannels.

24. A system for processing a microscale device, the system comprising:
   a manifold comprising a plurality of ring reservoirs in fluid contact with one or more mesoscale flush channels or one or more mesoscale waste channels, wherein two or more of the plurality of ring reservoirs are concentric and share a flowpath in one or more channel segments;
   one or more orifices in fluid contact with the flush channels or waste channels, and adapted to functionally contact one or more wells of the microscale device; and,
   a gas in a flowpath comprising the one or more mesoscale channels, the one or more orifices, and the one or more wells of the microscale device, wherein the flowpath comprises a pressure differential;
   whereby process solutions or waste solutions are flushed from the manifold, wells, or microfluidic device.

25. The system of claim 24, wherein the contact between the one or more orifices and the one or more wells comprises a sealed contact.

26. The system of claim 24, wherein the waste channel comprises a pressure less than atmospheric pressure.

27. The system of claim 24, wherein the pressure differential ranges from about 1 psi to about 500 psi.

28. The system of claim 24, wherein the flowpath further comprises one or more microchannels.

* * * * *